United States Patent
Johansson et al.

(10) Patent No.: US 6,287,330 B1
(45) Date of Patent: *Sep. 11, 2001

(54) AORTOILIAC GRAFTING SYSTEM AND METHOD

(75) Inventors: Peter K. Johansson, San Jose; Dinah B. Quiachon, Mountain View; Victor M. Bernhard, Menlo Park; Tammy L. Trayer, Belmont, all of CA (US); Richard S. Williams, Bussem (NL)

(73) Assignee: Endovascular Technologies, Inc., Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/978,066

(22) Filed: Nov. 25, 1997

Related U.S. Application Data

(63) Continuation-in-part of application No. 08/707,179, filed on Sep. 3, 1996, now Pat. No. 5,824,044.

(51) Int. Cl.$^7$ .................................................. A61F 2/06
(52) U.S. Cl. ...................... 623/1.13; 623/1.23; 606/194; 606/195
(58) Field of Search ................... 623/1, 12, 1.13, 623/1.23, 1.1; 606/191–198, 108, 194, 195

(56) References Cited

U.S. PATENT DOCUMENTS

| | | | |
|---|---|---|---|
| 3,657,744 | 4/1972 | Ersek | 128/334 |
| 4,061,134 | 12/1977 | Samuels | 128/1 |
| 4,108,161 | 8/1978 | Samuels | 128/1 |
| 4,140,126 | 2/1979 | Choudhury | 128/325 |

(List continued on next page.)

FOREIGN PATENT DOCUMENTS

| | | |
|---|---|---|
| 0 423 916 A1 | 4/1991 | (EP). |
| 0 461 791 A1 | 12/1991 | (EP). |
| 0 472 731 A1 | 3/1992 | (EP). |
| 0 667 132 A2 | 8/1995 | (EP). |
| WO 91/12047 | 6/1991 | (JP). |
| WO 95/16406 | 6/1995 | (WO). |
| WO 95/34255 | 12/1995 | (WO). |

OTHER PUBLICATIONS

MedPRO Month (Sample Issue 1993); Transcatheter Cardiovascular Therapy.

Mirich, David, M.D.; Radiology, vol. 170 No. 3 Part 2 (1989); pp. 1033–1037; Percutaneously Placed Endovascular Grafts for Aortic Aneurysms: Feasibility Study.

(List continued on next page.)

Primary Examiner—Corrine McDermott
Assistant Examiner—Choon P. Koh
(74) Attorney, Agent, or Firm—Fulwider Patton Lee & Utecht, LLP

(57) ABSTRACT

An aortoiliac intraluminal grafting system incorporating novel structural features for enhancing the effective and efficient deployment of a tapered prosthesis having at least one attachment system, in the vessel of an animal body, the system including a balloon catheter assembly, an inferior capsule catheter assembly, a superior capsule assembly and means interacting therewith, and a capsule jacket assembly. The capsule assemblies include an inferior capsule and a superior capsule, wherein the attachment systems of the tapered prosthesis are disposed within the two capsules. The tapered prosthesis embodies a main tubular member and an inferior tubular portion, having attachment systems secured to the superior end of the main tubular member and the inferior end of the inferior tubular portion. An occlusive device and deployment catheter is also disclosed. The occlusive device is used where it is desirable to occlude specific body lumens and can be used in combination with the tapered graft to repair a patient's vasculature near a bifurcation.

55 Claims, 18 Drawing Sheets

U.S. PATENT DOCUMENTS

| | | | |
|---|---|---|---|
| 4,441,215 | 4/1984 | Kaster | 3/1.4 |
| 4,512,338 | 4/1985 | Balko et al. | 128/1 |
| 4,562,596 | 1/1986 | Kornberg | 623/1 |
| 4,577,631 | 3/1986 | Kreamer | 128/334 |
| 4,580,568 | 4/1986 | Gianturco | 128/345 |
| 4,617,932 | 10/1986 | Kornberg | 128/334 |
| 4,655,771 | 4/1987 | Wallsten | 623/1 |
| 4,681,110 | 7/1987 | Wiktor | 128/343 |
| 4,733,665 | 3/1988 | Palmaz | 128/343 |
| 4,739,762 | 4/1988 | Palmaz | 128/343 |
| 4,740,207 | 4/1988 | Kreamer | 623/1 |
| 4,776,337 | 10/1988 | Palmaz | 128/343 |
| 4,787,899 | 11/1988 | Lazarus | 623/1 |
| 4,830,003 | 5/1989 | Wolff et al. | 128/343 |
| 4,872,874 | 10/1989 | Taheri | 623/1 |
| 5,078,726 | 1/1992 | Kreamer | 606/194 |
| 5,078,735 | 1/1992 | Mobin-Uddin | 623/1 |
| 5,104,399 | 4/1992 | Lazarus | 623/1 |
| 5,151,105 | 9/1992 | Kwan-Gett | 623/1 |
| 5,201,757 * | 4/1993 | Heyn et al. | 606/198 |
| 5,207,695 | 5/1993 | Trout | 606/153 |
| 5,211,658 | 5/1993 | Clouse | 623/1 |
| 5,219,355 * | 6/1993 | Parodi et al. | 606/191 |
| 5,236,446 | 8/1993 | Dumon | 623/1 |
| 5,275,622 * | 1/1994 | Lazarus et al. | 623/1 |
| 5,282,824 | 2/1994 | Gianturco | 606/198 |
| 5,316,023 | 5/1994 | Palmaz et al. | 128/898 |
| 5,360,443 | 11/1994 | Barone et al. | 623/1 |
| 5,383,926 | 1/1995 | Lock et al. | 623/1 |
| 5,387,235 | 2/1995 | Chuter | 623/1 |
| 5,425,765 | 6/1995 | Tiefenbrum et al. | 623/12 |
| 5,453,090 | 9/1995 | Martinez et al. | 604/53 |
| 5,456,713 | 10/1995 | Chuter | 623/1 |
| 5,460,170 | 10/1995 | Hammerslag | 600/201 |
| 5,464,449 | 11/1995 | Ryan et al. | 623/1 |
| 5,507,769 | 4/1996 | Marin et al. | 606/198 |
| 5,522,880 | 6/1996 | Barone | 623/1 |
| 5,527,355 | 6/1996 | Ahn | 623/1 |
| 5,562,724 | 10/1996 | Vorwerk et al. | 623/1 |
| 5,562,726 | 10/1996 | Chuter | 623/1 |
| 5,571,170 | 11/1996 | Palmaz et al. | 623/1 |
| 5,571,171 | 11/1996 | Barone et al. | 623/1 |
| 5,571,172 | 11/1996 | Chin | 623/1 |
| 5,571,173 | 11/1996 | Parodi | 623/1 |
| 5,575,817 | 11/1996 | Martin | 623/1 |
| 5,656,036 * | 8/1997 | Palmaz | 623/12 |
| 5,755,773 * | 5/1998 | Evans et al. | 623/1 |
| 5,782,909 * | 7/1998 | Quiachon et al. | 623/1 |
| 5,824,044 | 10/1998 | Quiachon | 623/1 |

OTHER PUBLICATIONS

Cragg, Andrew H., M.D.; Interventional Radiology, vol. 150 No. 1 (1983); pp. 45–49; Percutaneous Arterial Grafting.

Dotter, Charles T., M.D.; Technical Developments and Instrumentation; pp. 259–260; Transluminal Expandable Nitinol Coil Stent Grafting: Preliminary Report.

Palmaz, Julio C., M.D.; Surgery (Feb. 1986); pp. 199–205; Expandable Intraluminal Vascular Graft: A Feasibility Study.

Lawrence, David D., M.D.; Cardiovascular Radiology (1987); pp. 357–360; Percutaneous Endovascular Graft: Experimental Evaluation.

Inoue, Kanji et al.; *Circulation* 1991, 84 (4 Suppl. II); II–421; Percutaneous Implantation of Aortic Endovascular Graft for Created Aneurysm: Animal Experiment.

Matsumae, Masaru, M.D.; Journal of Vascular Surgery (1988); pp. 38–44; An Experimental Study of a New Sutureless Intraluminal Graft with an Elastic Ring that Can Attach Itself to the Vessel Wall.

Maass, D.; RSNA (1984); pp. 659–663; Radiological Follow–Up of Transluminally Inserted Vascular Endoprostheses: An Experimental Study Using Expanding Spirals.

Dotter, Charles T., M.D.; Investigative Radiology (1969); pp. 329–332; Transluminally–Placed Coilspring Endarterial Tube Grafts.

Cragg, Andrew, M.D.; Radiology (1983); pp. 261–263; Nonsurgical Placement of Arterial Endoprostheses: A New Technique Using Nitinol Wire.

* cited by examiner

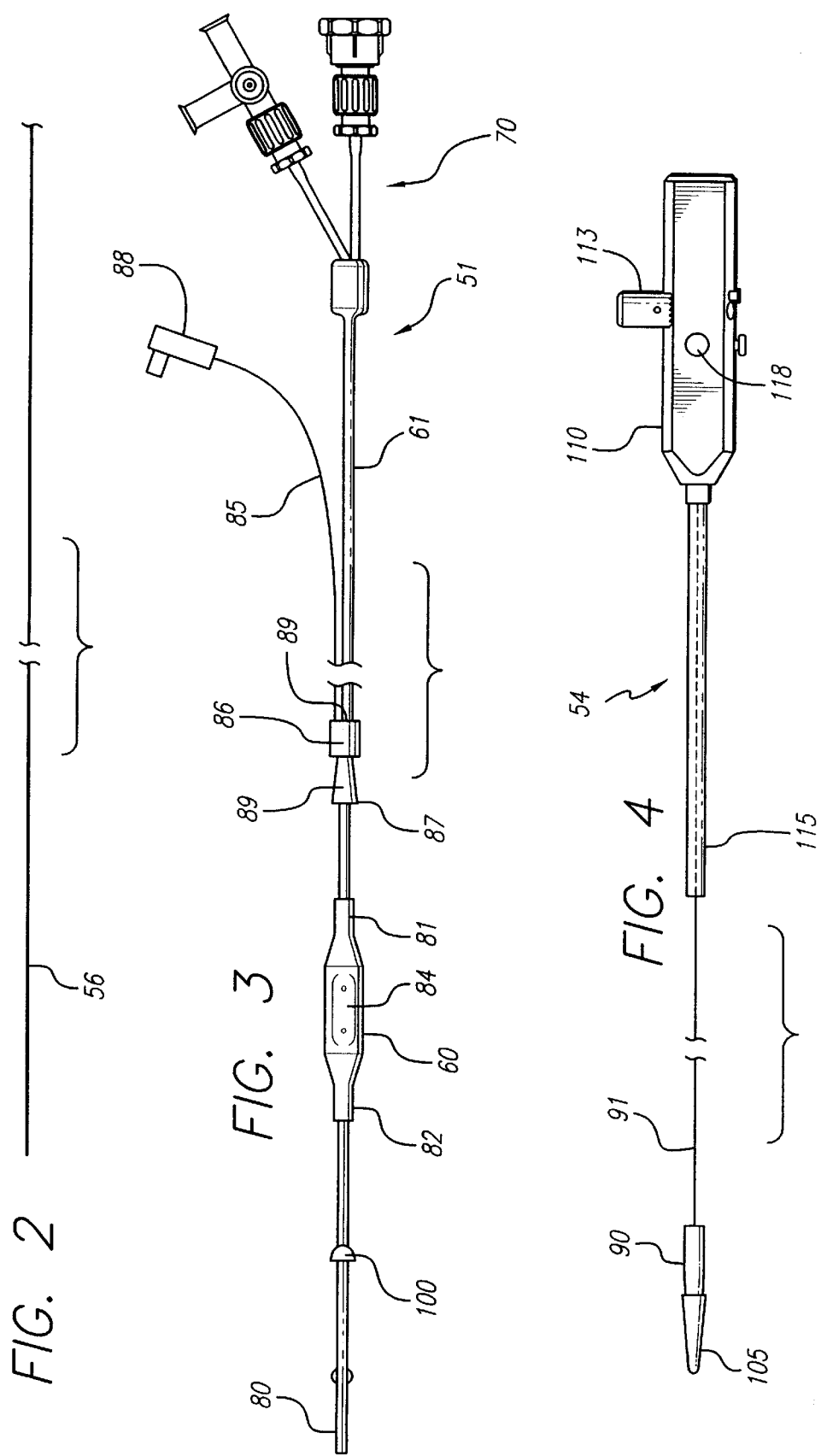

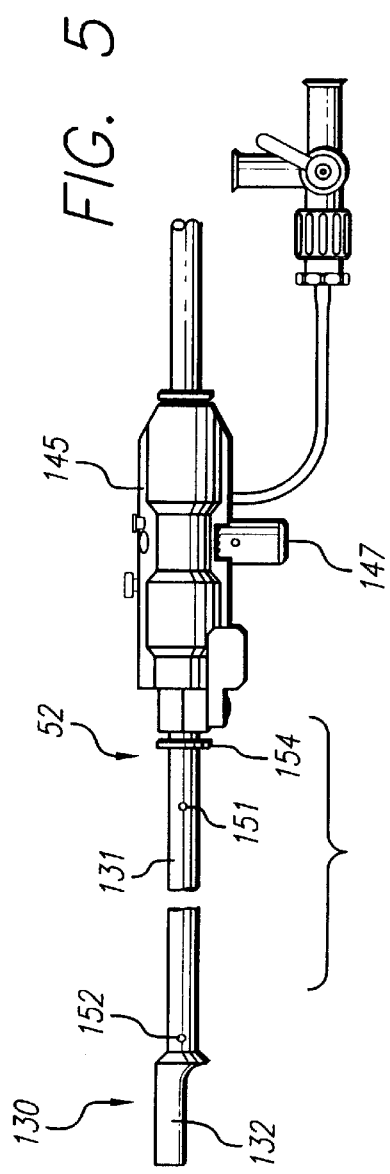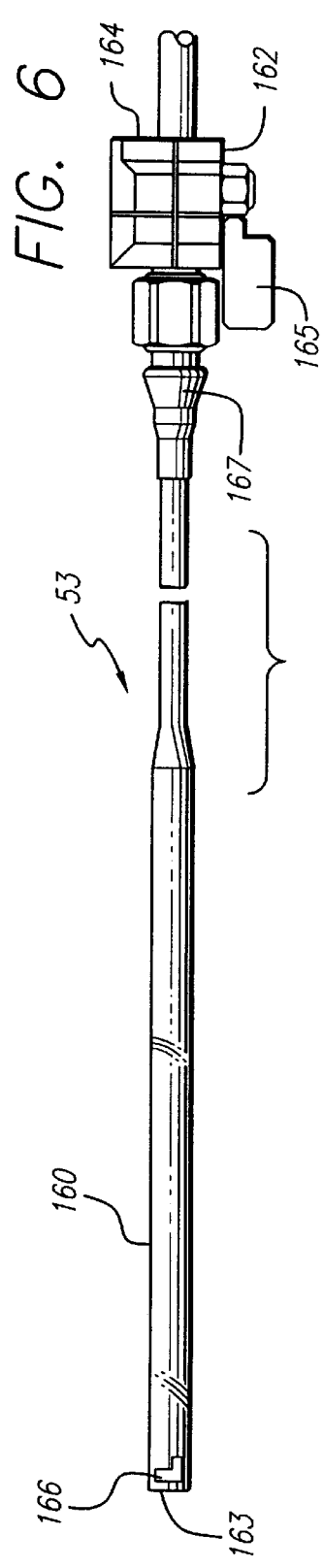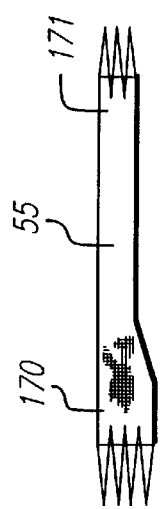

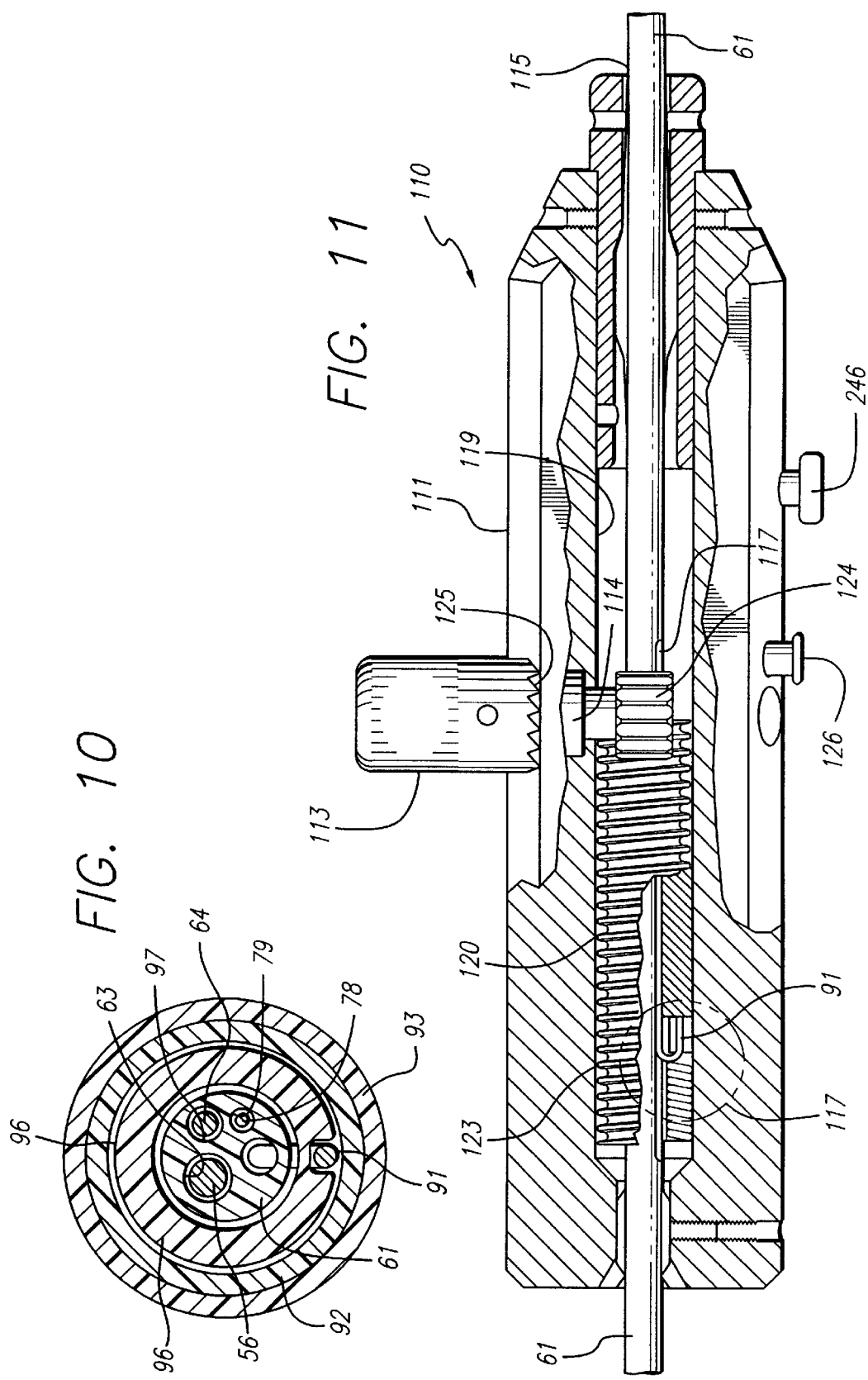

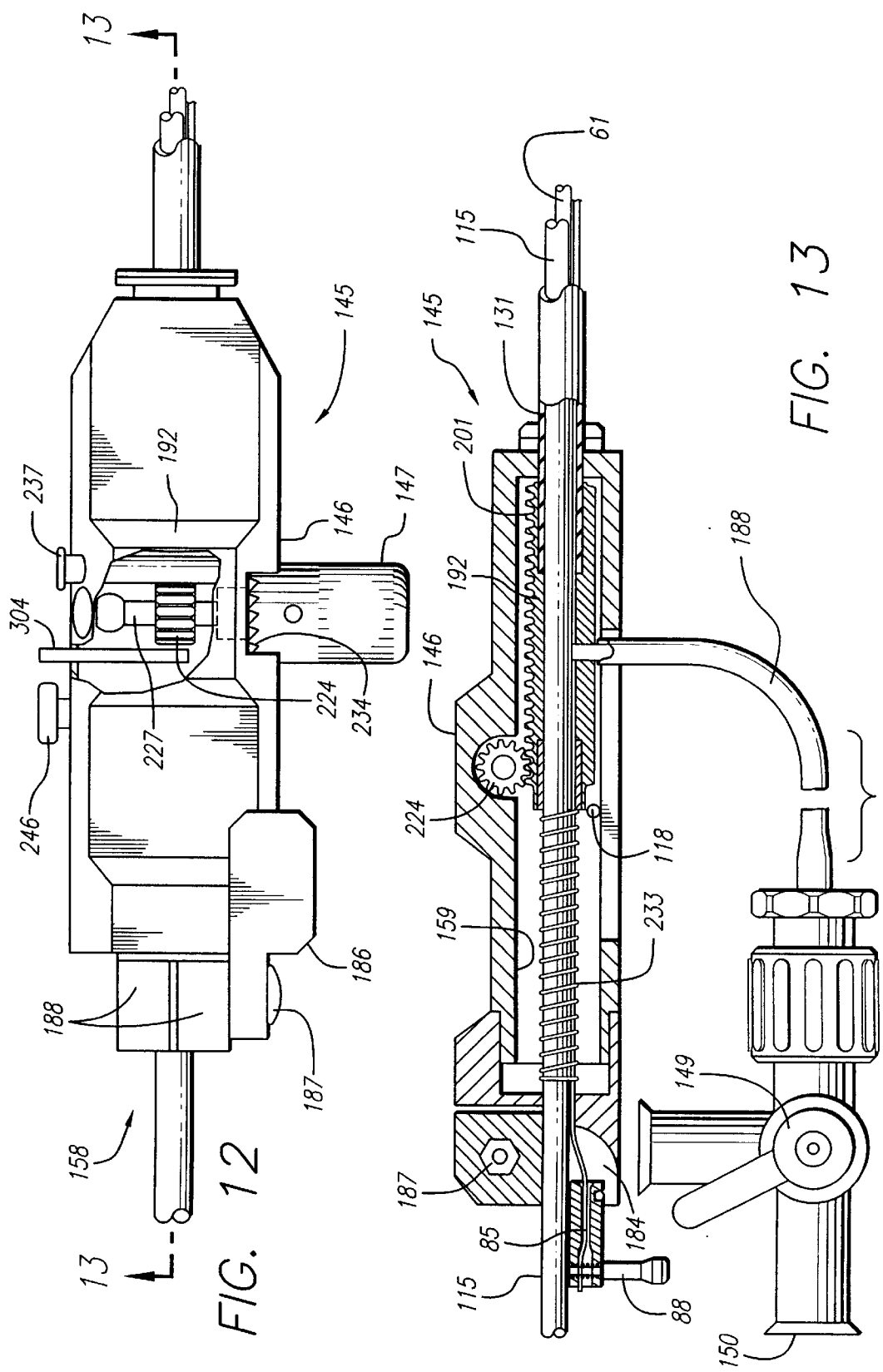

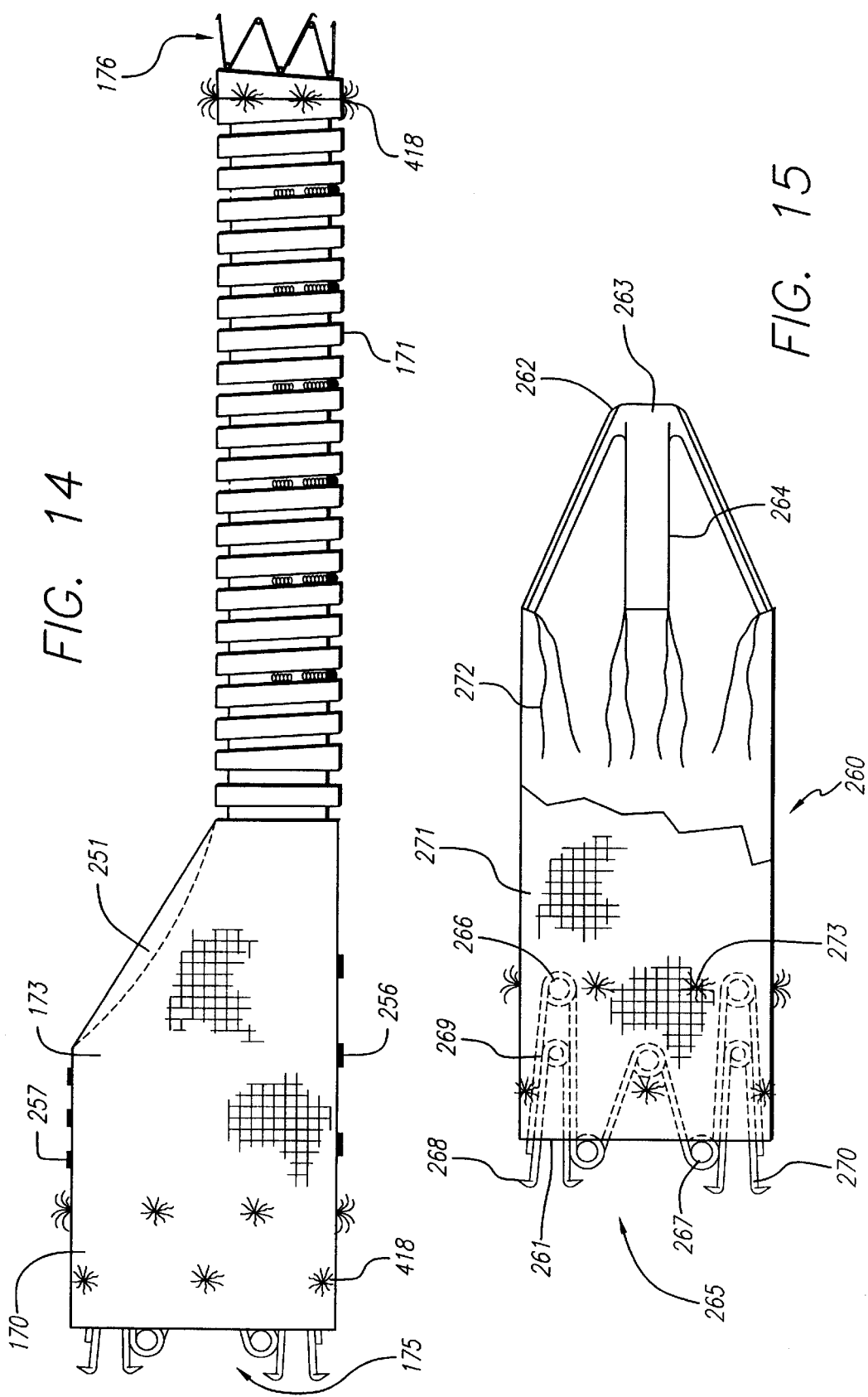

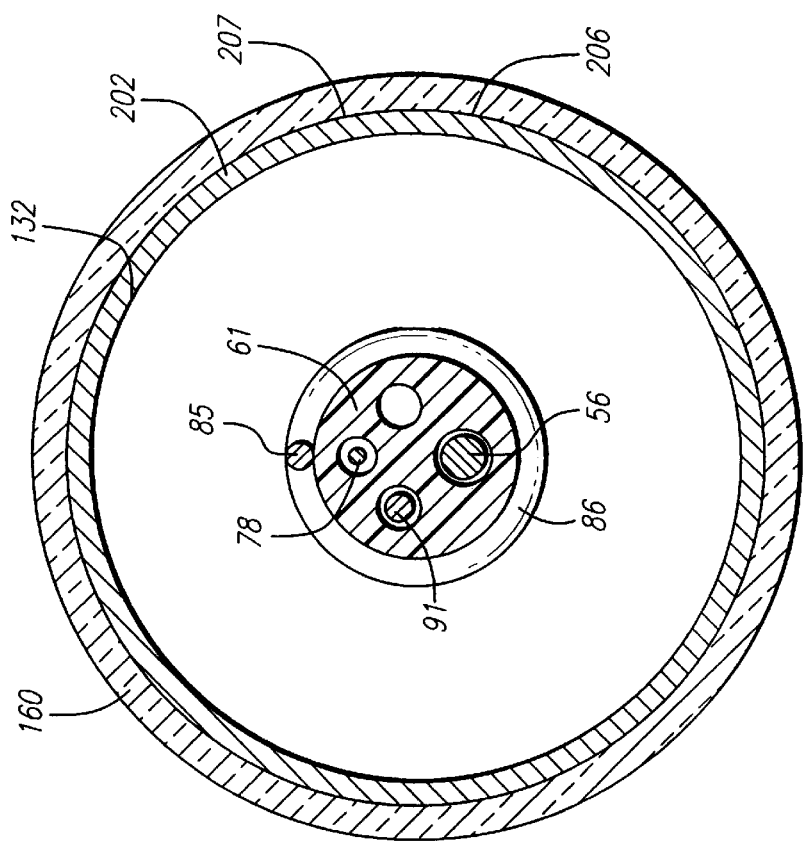
FIG. 25
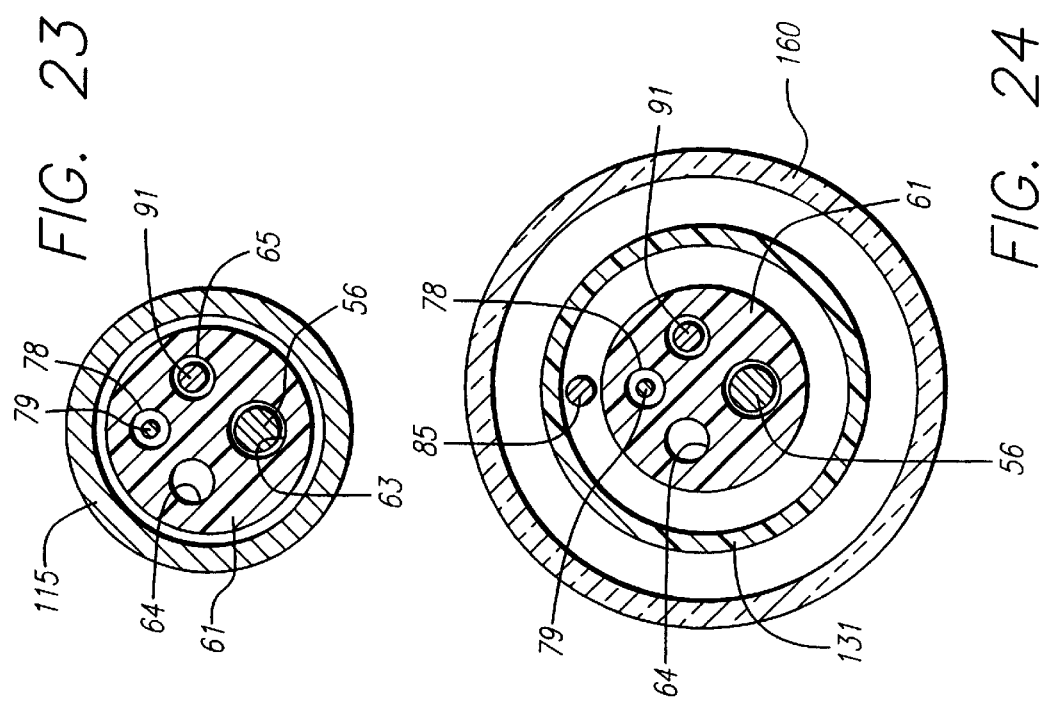
FIG. 23
FIG. 24

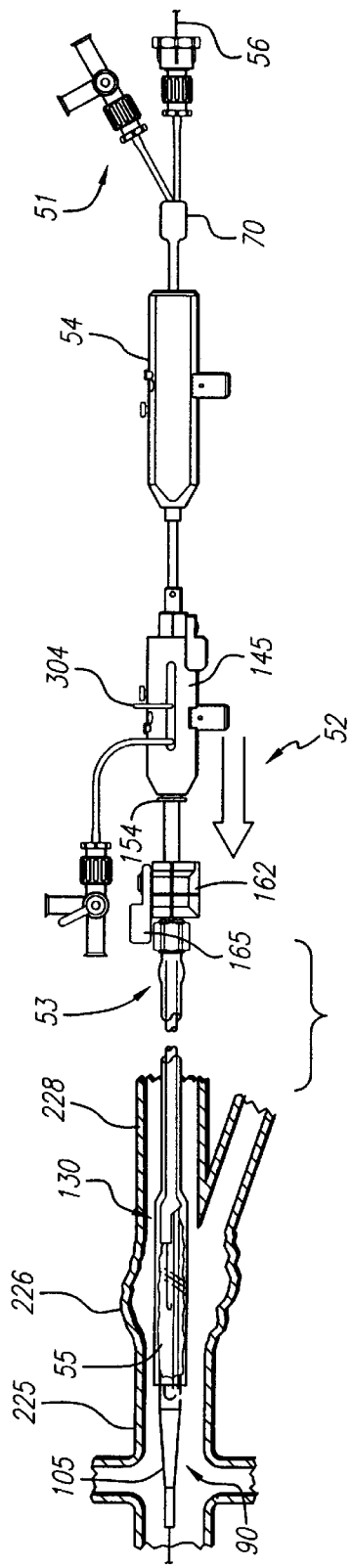
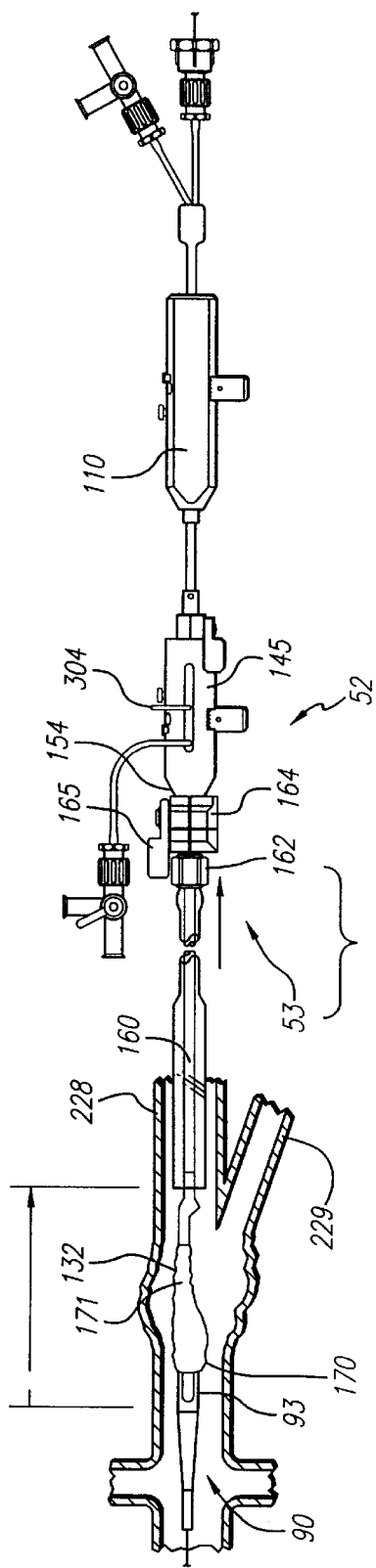
FIG. 26
FIG. 27

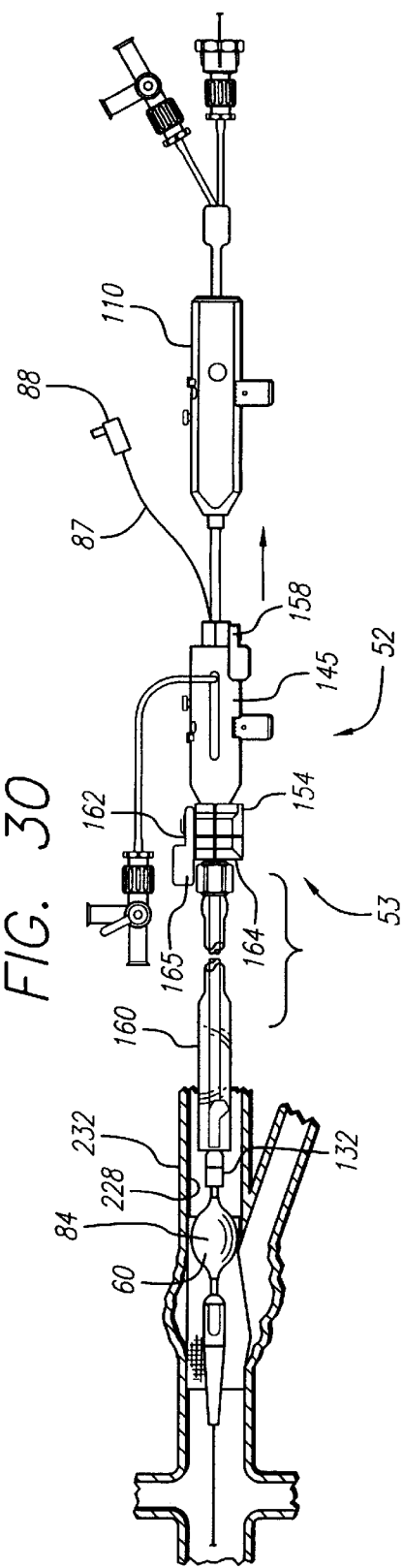
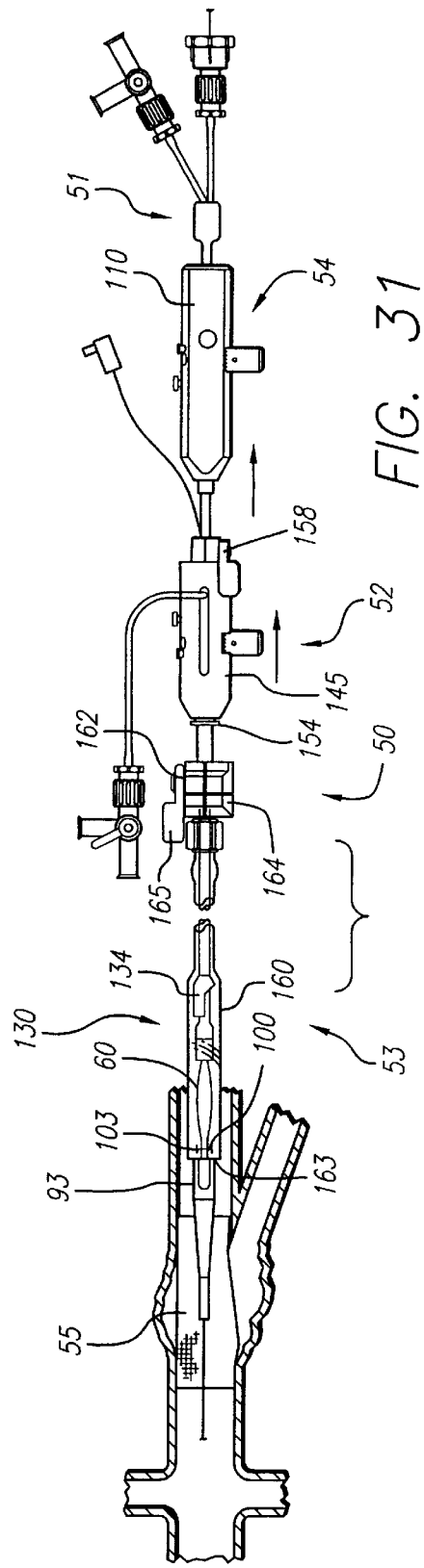

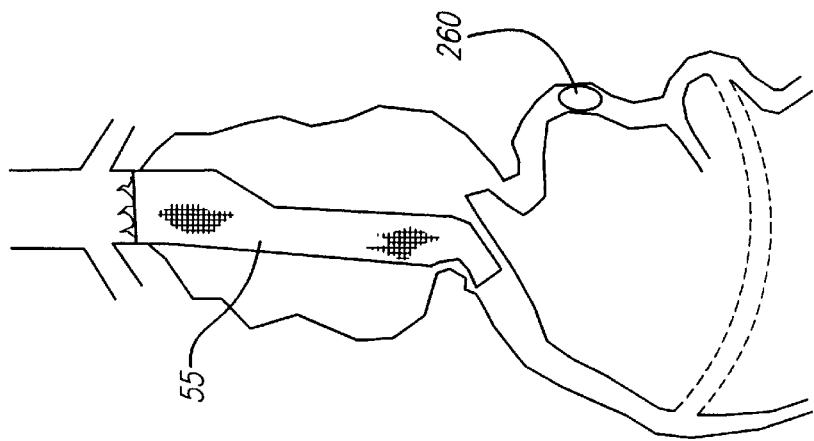
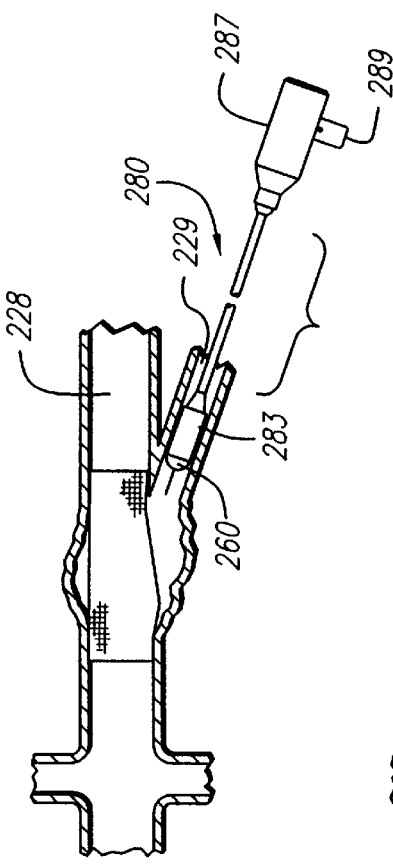
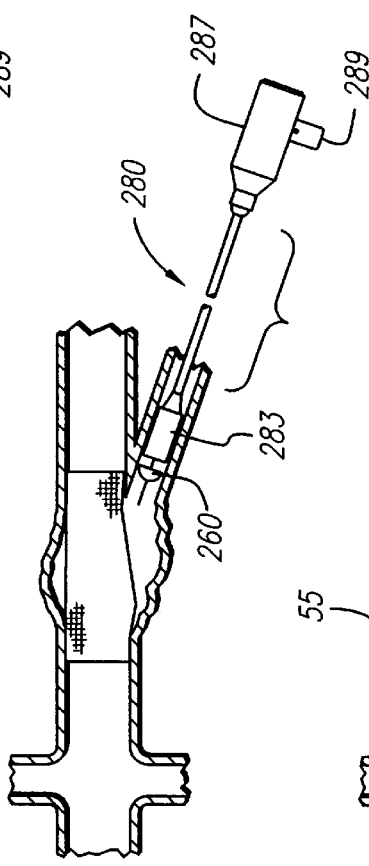
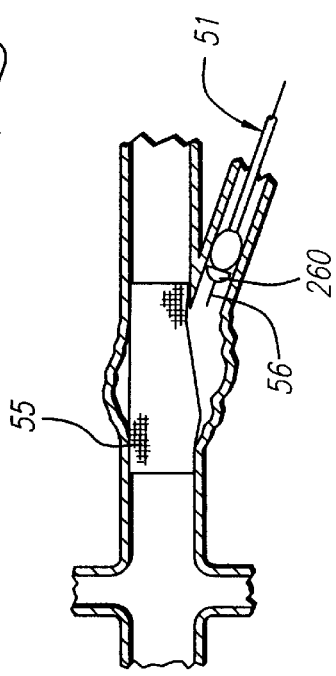

AORTOILIAC GRAFTING SYSTEM AND METHOD

CROSS-REFERENCES TO RELATED APPLICATIONS

This application is a continuation-in-part of application Ser. No. 08/707,179, filed Sep. 3, 1996 now U.S. Pat. No. 5,824,044. The contents of that application is hereby incorporated herein by reference.

BACKGROUND OF THE INVENTION

This invention relates to a system and method for emplacing a repair device within a patient's vasculature and, more particularly, to a delivery catheter and method of use for placement within a corporeal lumen of a tapered graft having one or more attachment systems.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and in turn may be life-threatening. In some cases, the damaged lumen is repairable only with the use of prosthesis such as an artificial vessel or graft.

For repair of vital vessels such as the aorta, surgical repair is significantly life-threatening. Surgical techniques known in the art involve major surgery in which a graft resembling the natural vessel is spliced into the diseased or obstructed section of the natural vessel. Known procedures include surgically bypassing the damaged or diseased portion of the vessel and inserting an artificial or donor graft attached to the native vessel by an anastomosis.

It is also known within the art to provide a repair device or prosthesis for intraluminal repair of a vessel, such as an abdominal aorta having an aneurysm. The art has taught to provide a prosthesis positioned in a vessel then securing the prosthesis within the vessel with hooks or staples that are mechanically extended by the user. The early prior art devices were large in diameter, mechanically complex and in turn were susceptible to mechanical failure. Prior intraluminal grafting systems have embodied capsule catheters or balloon catheters, but were relatively stiff and of a relatively high profile. Similarly, the prior art systems were configured in such a way that the graft was relatively difficult to deploy in the correct position. In addition, prior systems having a capsule catheter assembly were usually configured such that the prosthesis was disposed within a unitary capsule. Further, the prior prostheses were sometimes ill suited to withstand the high pressures existing in the vessels and, consequently, experienced structural failures.

Where the deteriorative disease occurs near a bifurcation, conventional tube and bifurcated grafts often cannot be used to repair the site. There may be insufficient room to implant an inferior end of a conventional tube graft near the bifurcation. Additionally, one branch of the bifurcation could be so diseased that a leg of a conventional bifurcated graft may be too large or small so that implant is impossible. Also, one branch of the bifurcation can be so diseased that blood through that branch should be blocked entirely and a different route provided.

Generally speaking, intraluminal repair of vessels or body lumens, where it is a viable alternative, can be performed with less threat to a patient. Moreover, since intraluminal repair does not require major surgery, the recovery time from such a procedure is usually shorter. However, in order to fully take advantage of the benefits of an intraluminal repair procedure, the system for accomplishing the same must be optimized to efficiently and effectively place a prosthesis within the vessel or lumen and include component parts which can be utilized in the situation where one branch of a bifurcation is so diseased that it is desirable to block it and provide an alternative route for blood flow through other surgical techniques such as a bypass. Furthermore, the prosthesis itself must be optimally configured so that it can withstand and adapt to the environment in which it is placed, as well as be specially equipped to repair a patient's vasculature near a diseased bifurcation. Accordingly, there is a need for the system to be configured such that advancement and deployment of the prosthesis and any auxiliary component parts can be accomplished in an efficient manner and such that the prosthesis can be accurately placed so that the attempted repair is effective. Additionally, there is a need for a prosthesis which itself is specifically configured for the environment existing within the vessel or lumen in which it is placed. Moreover, there exists a need for a grafting system which repairs diseased vessels in the situation where conventional tube and bifurcated grafts are found lacking. The present invention addresses these needs.

To provide consistency with the common usage of terms used in the medical surgical arts in the United States, the terms "proximal, distal, inferior and superior" are used with a certain regularity within the present specification. Proximal refers to parts of the system, such as catheters, capsules and wires, which are closest to the user and closest to the portion of the system outside or exterior of the patient. Distal refers to the point farthest from the user and typically most interior to the corporeal lumen. The term superior refers to a location situated above and is used herein in description of the graft and attachment system as well as the components of the delivery system. Inferior refers to the point situated below and again is used herein with the graft, attachment system and delivery system. Thus, for applications in the abdominal aorta which use a femoral approach, the superior end of the graft resides within the most distal or superior portion of the delivery catheter. Likewise, the inferior end of the graft resides within the inferior or proximal capsule which is on the most distal or superior portion of the capsule catheter.

The term "ipsilateral" typically refers to a vessel or part of a device which resides on the same side in which a device enters a lumen. Similarly, the term "contralateral" refers to a vessel or device residing on the opposite side of which the main device enters, for example, the iliac or femoral arteries.

SUMMARY OF THE INVENTION

Briefly, and in general terms, the present invention provides an aortoiliac grafting system for securing a repair device within or between vessels or corporeal lumens of an animal, such as a human. The preferred embodiment of the placement system is configured for introducing a graft or prosthesis into a corporeal lumen and positioning the graft in the area of the aortic bifurcation.

Basically, the present invention is directed to a system and method for implanting a tapered prosthesis or graft utilizing a catheter assembly having a multiplicity of capsules. The delivery system includes a balloon catheter assembly, a superior capsule assembly, an inferior capsule catheter assembly, and a capsule jacket assembly. The system also includes control wire and locking wire assemblies. Also provided is an occlusive device and a deployment system therefor.

The prosthesis comprises a tapered graft having a self-expanding attachment system at each of its superior and inferior ends. In certain applications, the prosthesis has an attachment system only at its superior end. Each attachment system is contained within its own compact capsule assembly during deployment. The capsule assemblies are movable relative to each other to allow the graft to be emplaced at the desired location in the corporeal lumen. The graft and capsules are deployed by a catheter assembly designed for traversing the femoral, iliac and aortic vessels of a human anatomy.

The occlusive device embodies a windsock configuration which includes an attachment system configured within its open end. The occlusive device can be used to prevent back flow as well as to occlude flow through a severely diseased branch of a bifurcation. The delivery system for the occlusive device includes a third capsule catheter assembly and a pusher button assembly.

The present system has several advantages over prior art systems. In particular, the present system incorporates various novel structural features which enhance the efficiency of the system as well as facilitates the effective deployment of the prosthesis within a vessel or body lumen. Moreover, the present system embodies a design which is optimized for ease of operation and manufacturability. Additionally, the system includes various advancements which also enhances its overall effectiveness.

More particularly, the tapered graft is configured such that it can be used to repair a vessel that is diseased at its bifurcation. The tapered graft is configured within the main lumen and extends into one branch of the bifurcation. Where appropriate, the occlusive device is placed within the other severely diseased branch in order to close it off and to prevent backflow. Standard surgical techniques are used to route a portion of the blood flow from the branch in which the tapered graft is placed to a point downstream of the occlusive device in the branch blocked by the occlusive device.

Additionally, the inferior capsule catheter assembly includes a handle embodying a rack and pinion device which is configured coaxially with the inferior capsule catheter tubular member in order to provide precise control as well as includes a conveniently assessable swing lock for engaging the balloon catheter shaft. The capsule jacket assembly includes a capsule jacket having a more easily manufacturable one-piece design and in a preferred embodiment, it is constructed from LDPE material.

The new and improved distal or superior capsule assembly includes a superior end configured with a nose cone for improved maneuverability of the intraluminal delivery system within vessels or corporeal lumens, as well as for providing a gradual transition of the overall profile of the delivery system. The control wire assembly also includes a handle having a more manufacturable single piece design and embodies a rack and pinion device which is configured coaxially with the control wire for more precise control.

The lock wire assembly is provided with an inferior lock spaced-apart from a pusher button which can be manipulated such that the inferior end of the prosthesis can be deployed in tension or compression. Also, the inferior end of the locking wire assembly includes a handle shaped so that it can be manipulated more conveniently. The superior end of the prosthesis and the occlusive devices are each provided with an attachment system embodying V-shaped members with hooked terminal ends which cooperate with a generally sinusoided frame to seat the superior end of the prosthesis and the occlusive devices within a vessel or lumen. This attachment system is optimally configured to be effective even in harsh environments wherein significant stresses are placed upon the members comprising the attachment system. Significantly, the number of connecting points among the various members of the superior attachment have been minimized. The inferior attachment system of the tapered graft includes a sinusoidal frame with a plurality of wall engaging members.

The new and improved procedure for manipulating the intraluminal delivery system to thereby deploy the prosthesis or graft within a vessel or lumen necessarily takes advantage of the various novel structural features incorporated into the delivery system. In particular, additional steps are contemplated to accomplish deploying the prosthesis either in tension or compression.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 2 is a side plan view of a guidewire to be used with the grafting system of the present invention.

FIG. 3 is a side plan view of the balloon catheter and locking wire of the present invention.

FIG. 4 is a side plan view of the superior capsule, control wire, hypotube and control wire handle assembly of the present invention.

FIG. 5 is a side plan view of the inferior capsule and inferior capsule catheter assembly of the present invention.

FIG. 6 is a side plan view of the capsule jacket assembly of the present invention.

FIG. 7 is a top plan view of a tapered graft.

FIG. 10 is a cross-sectional view taken along the line 10—10 of FIG. 9.

FIG. 11 is a partial cross-sectional view of the control wire and control handle mechanism shown in FIG. 4.

FIG. 12 is an enlarged side perspective view of the inferior capsule handle.

FIG. 13 is a cross-sectional view of FIG. 12 taken along line 13—13 of FIG. 12.

FIG. 14 is an enlarged top plan view of a tapered graft of the present invention.

FIG. 15 is an enlarged partial cross-section view of an occlusive device of the present invention.

FIG. 23 is a cross-sectional view taken along the line 23—23 of FIG. 1.

FIG. 24 is a cross-sectional view taken along the line 24—24 of FIG. 1.

FIG. 25 is a cross-sectional view taken along the line 25—25 of FIG. 8.

FIG. 26 is a partial cross-sectional view of the intraluminal grafting system shown positioned within the corporeal lumen.

FIG. 27 is a partial cross-sectional view of the intraluminal grafting system, wherein the capsule jacket has been withdrawn from the graft.

FIG. 30 is a partial cross-sectional view of the intraluminal grafting system, wherein the inflatable member of the balloon catheter has been moved and inflated proximate the inferior attachment system of the tapered graft.

FIG. 31 is a partial cross-sectional view of the intraluminal grafting system, wherein the balloon catheter, capsule catheter and capsule jacket have been placed in a position for withdrawal from the corporeal lumen.

FIG. 32 is a partial cross-sectional view of the occlusive delivery system shown positioned within the corporeal lumen.

FIG. 33 is a partial cross-sectional view of the occlusive device deployed within the corporeal lumen.

FIG. 34 is a partial cross-sectional view of an inflatable member of a balloon catheter configured within the occlusive device.

FIG. 35 is a partial cross-sectional view of the tapered graft deployed within a patient's vasculature.

DESCRIPTION OF THE PREFERRED EMBODIMENTS

Figure 1:
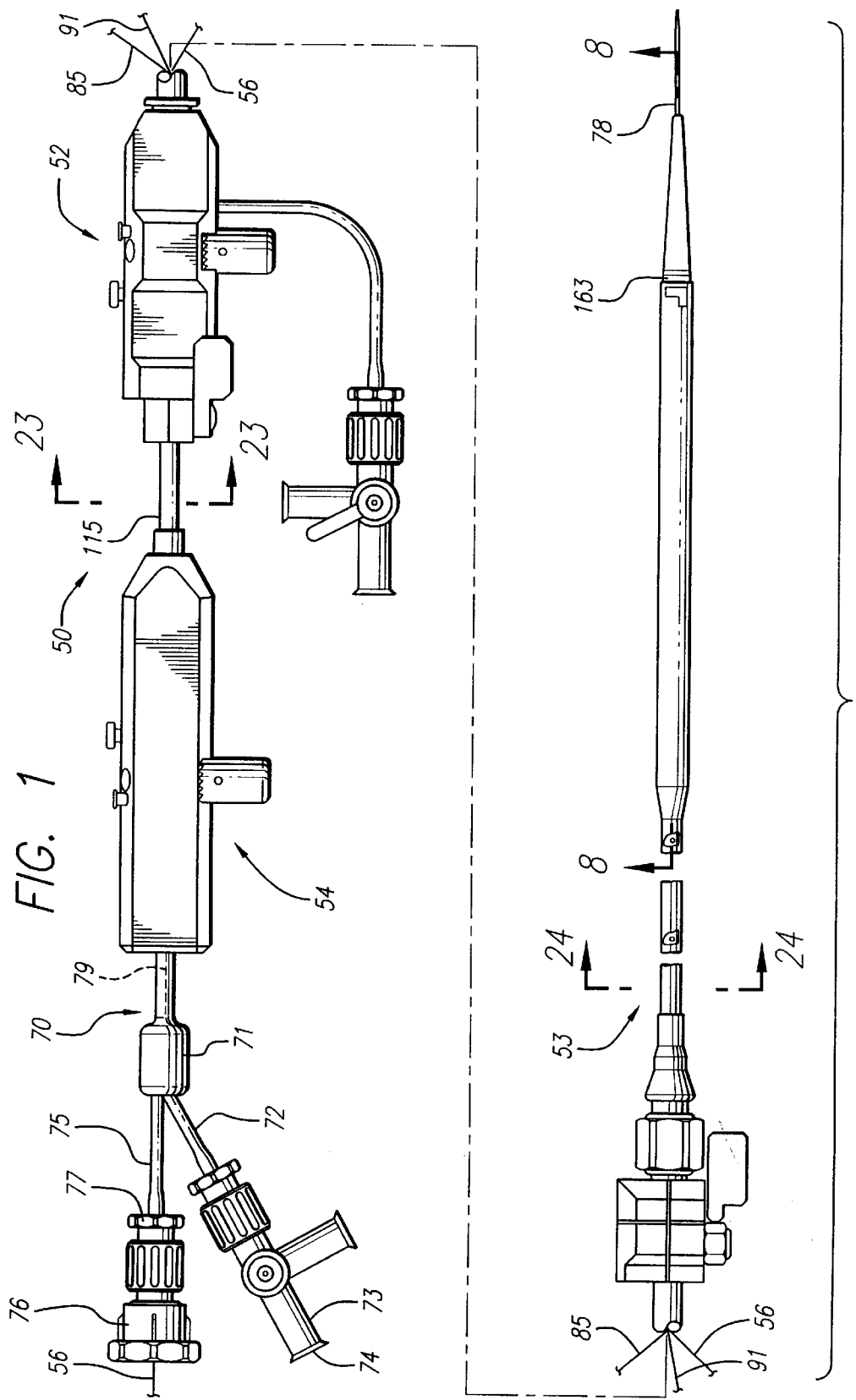
FIG. 1 is a side plan view of an aortoiliac intraluminal grafting apparatus and system incorporating the present invention.

As shown in the drawings and for purposes of illustration, the invention is embodied in an aortoiliac intraluminal grafting system of the type having a balloon catheter assembly, an inferior capsule catheter assembly, a superior capsule assembly and means interacting therewith, and a protective sleeve or capsule jacket. The novel features of the present system are directed towards enhancing the efficiency of the intraluminal grafting system, facilitating the effective deployment of a prosthesis within a vessel or body lumen and providing a system well suited for effectively repairing the vessel or lumen that is diseased at a bifurcation.

In the present system, the prosthesis or graft is comprised of a tapered body having superior and inferior extremities. The superior extremity of the graft comprises a main tubular member which tapers down to a more narrow inferior extremity of the graft. An attachment system is secured to the superior end of the main tubular member as well as to the inferior end of the graft. Each attachment system is provided with lumen piercing members which are covered during deployment by the superior and inferior capsule assemblies. The balloon catheter, capsule catheter and capsule jacket are configured coaxially so that relative movement between them provides for deployment of the graft. The inflatable member of the balloon catheter is used to firmly implant the attachment systems, and thereby the graft, in the lumen.

The present system further includes an occlusive device configured for placement in a severely diseased branch of a bifurcation and a system for deploying the occlusive device. The occlusive device embodies a windsock configuration with a self-expanding attachment system attached to its open end.

Figure 8:
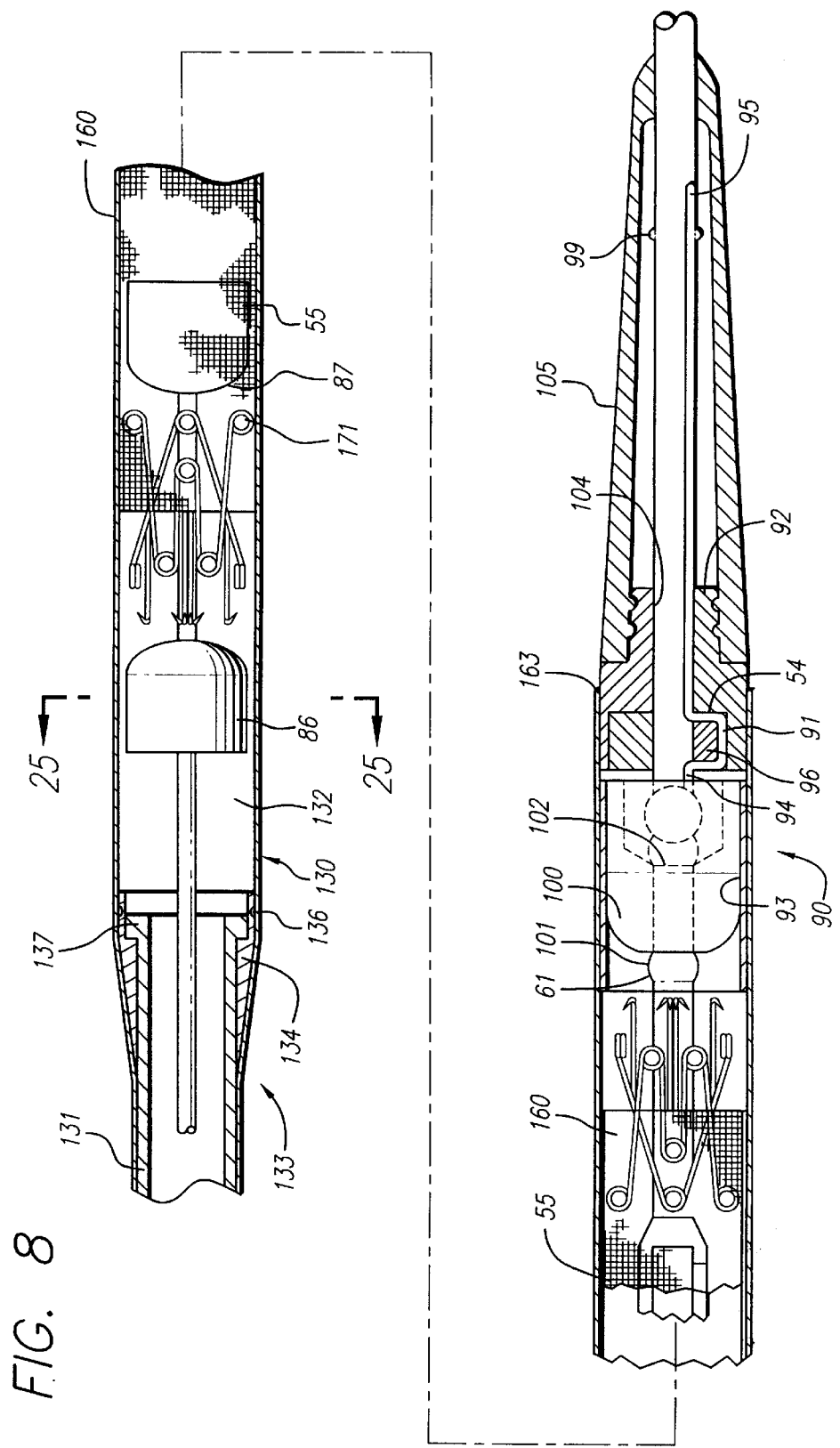
FIG. 8 is a partial cross-sectional view of the distal end of the intraluminal grafting apparatus and system along the line 8—8 of FIG. 1.

In more detail, the aortoiliac intraluminal grafting system 50 is shown in FIGS. 1–8. The system includes a balloon catheter assembly 51, which is coaxially disposed within inferior capsule catheter assembly 52, which is coaxially disposed within capsule jacket assembly 53. As shown in FIG. 8, the inferior or proximal capsule assembly 130 and superior or superior capsule assembly 90 are used to contain the tapered graft 55. A control wire assembly 54 is coaxially disposed within a lumen of the balloon catheter assembly and configured to move the superior capsule assembly in relation to the other system components. In the preferred embodiment, the system is used as an over-the-wire device, such that the balloon catheter is further configured with a lumen for a guidewire 56.

As shown in FIGS. 1 and 3, the aortoiliac intraluminal grafting system 50 also includes a balloon catheter assembly 51 which consists of an inflatable member or balloon 60 secured to a flexible elongate element or balloon catheter shaft 61. As shown in FIG. 23, the balloon catheter shaft is preferably configured with four lumens; however, the balloon catheter may be configured with a single, dual or triple, or similar multilumen shaft. A guidewire lumen 63 extends the length of the balloon catheter shaft. Similarly, a balloon inflation lumen 64 extends from the proximal end 70 of the balloon catheter to the inflatable member 60, wherein an inflation port (not shown), is provided to allow inflation fluid to enter and exit the inflatable member. The third lumen 65 is provided for a control wire 91. A fourth lumen 78 is provided for an anti-elongation reinforcement wire 79 made from kevlar fiber, stainless steel wire, or equivalent material. In the preferred embodiment, the reinforcement wire 79 extends the length of the balloon catheter shaft.

The flexible elongate element or balloon catheter shaft 61 is preferably formed of a material suitable for intraluminal use, such as irradiated polyethylene tubing. The four lumen balloon catheter shaft is preferably extruded to an outside diameter of 0.08 inches (2.03 mm). The guidewire lumen 63 has an inner diameter of 0.042 inches (1.07 mm). The inflation lumen 64 and the control wire lumen 65 have identical inner diameters of 0.022 inches (0.56 mm). The reinforcement wire lumen 78 is 0.009 inches. However, the lumen inside diameter may range from 0.006 to 0.06 inches (0.381–1.52 mm) and the outside diameter may range from 0.035 to 0.1 inches (0.889–2.54 mm) for a multilumen balloon catheter shaft. The balloon catheter may vary in length to suit the application, for example, from fifty to one hundred-fifty centimeters.

Referring to FIG. 1, the proximal extremity 70 of the balloon catheter shaft 61 is secured to a manifold adapter 71 which splits the guidewire lumen 63 from inflation lumen 64. The side arm 72 of the adapter 71 has a stop cock 73 mounted at its proximal end which is movable between open and closed positions. The stop cock is provided with a Luer fitting 74 which is adapted to be secured to a syringe for injecting inflation fluid. The side arm 75 of the manifold adapter 71 is connected to female Luer fitting 77 for distal tip injection and to a Touhy Borst adapter 76 which is configured to removably and slideably receive the guidewire 56. The reinforcement wire 79 is disposed and attached in the reinforcement wire lumen 78 between the manifold adapter and the control handle assembly 110 at the proximal end, and at its distal end near the distal extremity 80 of the balloon catheter shaft 61.

The inflatable member or balloon 60 is preferably secured twelve centimeters from the distal extremity 80 of the balloon catheter shaft 61. The balloon is positioned proximal of the superior capsule assembly 90 and the superior end of the graft 55. For shorter grafts of four to seven centimeters in length, the inflatable member may be positioned distal of the superior capsule assembly. The balloon is formed of suitable material such as polyethylene. The polyethylene utilized for the balloon is irradiated to achieve an appropriate balloon size. For larger diameter balloons, higher tensile strength materials like polyethyleneterephthalate (PET) is desirable because thinner walls, hence a lower profile, can be achieved.

The balloon can vary in diameter from twelve to forty-five millimeters in diameter and can have a wall thickness ranging from 0.001 to 0.005 inches (0.0254–0.127 mm). The preferred balloon made in accordance with the present invention has an outside diameter of 20 to 26 millimeters, a diameter slightly larger than the inner diameter of the graft, and has a wall thickness of approximately 0.003 inches (0.076 mm). The range may be 18 to 28 millimeters. In addition, the balloon is pleated along its axis for a low profile which facilitates its introduction into a corporeal lumen of a patient as hereinafter described. Further, the deflated balloon is heated to provide it with a memory of its low profile configuration.

The balloon catheter shaft 61 is provided with an inflation lumen 64 which is in fluid communication with the balloon 60. The inflation lumen is used to inflate and deflate the balloon 60 by introducing and withdrawing a gas or liquid through the inflation port. The balloon proximal stem 81 and balloon distal stem 82 are heat sealed to the balloon catheter shaft to form a fluid tight seal. The length of the proximal stem may vary from 0.5 to 1.0 centimeter.

Radiopaque markers are embedded in the balloon catheter shaft approximately two millimeters distal the balloon inflation port. The radiopaque marker is a platinum or tungsten coil one centimeter long with an outer diameter of 0.02 inches (0.508 mm) and is located proximate the center of the balloon 60. Preferably two radiopaque platinum marker bands, 8 millimeters apart, with an outer diameter of 0.080 are positioned over the balloon catheter shaft 61 and are located proximate the center of the balloon 60. A strain relief or support wire may be disposed in the inflation lumen 64 between the distal end 80 of the balloon catheter shaft and the balloon distal stem 82 if a three lumen balloon catheter is used.

It should be appreciated that although a separate inflatable member has been described, an integral coaxial inflatable member may be provided which is formed of the same tubing from which the balloon catheter shaft is made. This can be readily accomplished, as is well known to those skilled in the art, by using an additional radiation dose for the balloon region of the shaft.

The balloon 60 can also be observed under x-rays if carbon dioxide is used as the inflation medium, because the blood in the patient's vessel is more opaque than the gas used for inflating the balloon. In addition, increased visibility of the balloon can be obtained by inflating the balloon with a diluted radiopaque contrast solution. Moreover, radiopaque bands of a suitable material such as platinum, gold or a platinum-tungsten alloy can be placed on the proximal and distal balloon stems 81 and 82 to aid in ascertaining the position of the balloon. Similarly, radiopaque rods may be inserted in the balloon inflation lumen.

As shown in FIGS. 1, 3 and 8, the locking wire 85 runs parallel to the balloon catheter graft 61 within the inferior capsule catheter assembly 52. The distal end of the locking wire may be configured with a proximal pusher button 86 and a distal lock button 87 secured approximately twelve millimeters apart. The radiopaque buttons are oblong shaped and include thru-holes 89 which slideably receive balloon catheter shaft 61. The buttons are disposed within the distal end of the inferior capsule catheter assembly during deployment and secure the attachment system attached to the inferior end of the tapered graft 55 within the distal end of the capsule catheter assembly.

The proximal end of the inferior end locking wire 85 extends through the proximal end of the inferior capsule catheter assembly 52. The proximal extremity of the locking wire is specially configured with a handle 88 which is configured for gripping. The locking wire handle is used to laterally move the radiopaque proximal button 86 and distal pusher lock button 87 which engage the attachment system attached to the inferior or proximal end of the graft 55. Rotation of the knob 147 (see FIG. 5) permits retraction of the inferior capsule to expose the inferior attachment system which is held fixed relative to the correal lumen via the lock 87 and pusher button 86. Movement of the locking wire handle in relation to the inferior capsule catheter assembly permits removal of the lock and pusher button back into the capsule catheter assembly after the deployment of the inferior attachment system.

The intraluminal grafting apparatus also includes a control wire assembly 54, which is shown in FIGS. 1 and 4. The superior distal end of the control wire assembly consists of a distal capsule assembly 90. As shown in more detail in FIGS. 8–10, the superior distal capsule assembly comprises a control wire 91 disposed within a superior distal cap 92 and superior distal cap spacer 96 disposed within the distal cap. The distal cap spacer is secured to the distal cap by means of an adhesive, solvent bonding, ultrasonic welding or by heat shrinking. A hollow superior or distal capsule 93 is secured to the distal cap and coaxially surrounds the control wire and balloon catheter shaft 61. The superior end of the distal cap is secured to nose cone 105 which provides the delivery system with improved maneuverability through vasculature due to its gradually tapered profile. Preferably, the nose cone 106 is formed of a low durometer plastic material such as polyester block amide under the trademark "PEBAX" with Bismuth Subcarbonate or barium sulphate for radiopacity.

The control wire 91 is slideably disposed in the control wire lumen 65. A longitudinal slot 94 is cut out of the balloon catheter shaft 61 to expose the control wire lumen and the control wire. To secure the control wire within the superior distal capsule assembly 90, the control wire is configured between the superior cap 92 and the superior cap spacer 96. The control wire is formed in a U-shaped bend over the superior cap spacer and is configured to slide within the slot and the control wire lumen of the balloon catheter shaft. The distal end 95 of the control wire resides in the portion of the control wire lumen beyond the distal end of the slot.

Figure 9:
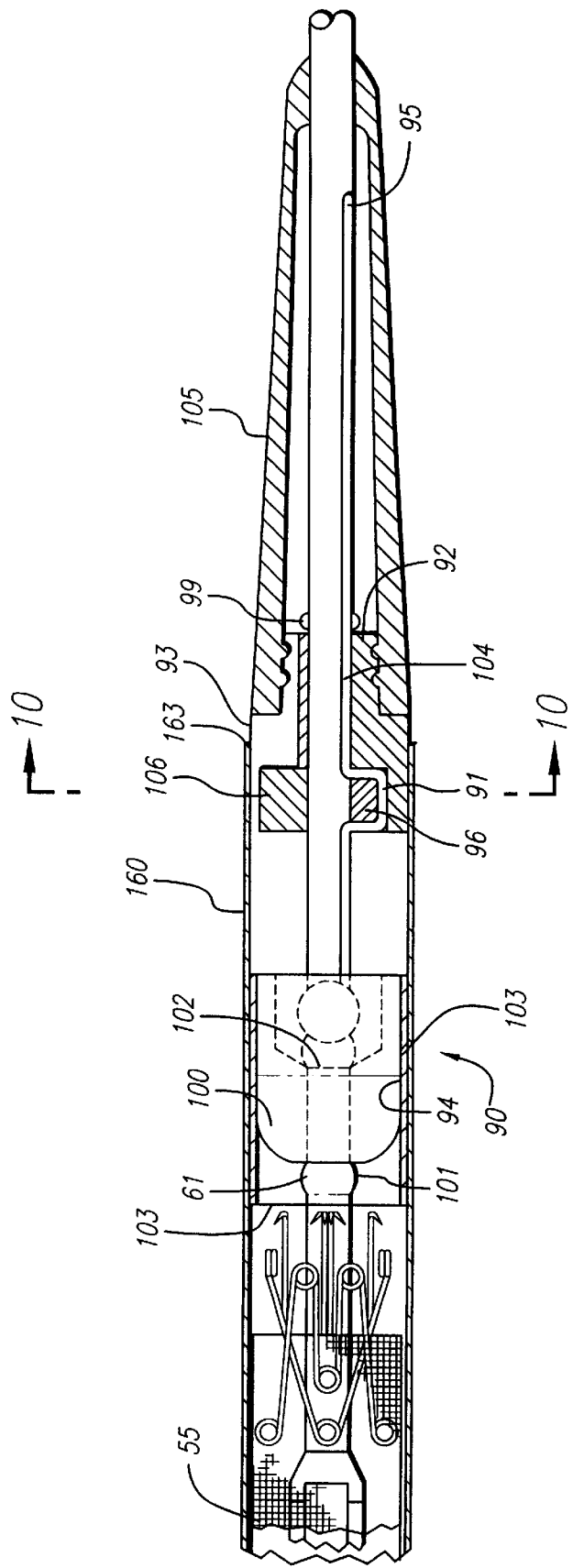
FIG. 9 is the partial cross-sectional view of FIG. 8, with the superior capsule and control wire moved proximally with respect to the balloon catheter.

The configuration shown in FIGS. 8–10 allows the superior cap assembly to move axially along the balloon catheter shaft. The U-shaped bend of the control wire over the superior cap spacer 96, however, prevents the superior cap assembly from rotating in relation to the balloon catheter shaft. As described above, the superior cap spacer is firmly secured within the superior cap 92. To prevent rotation of the superior cap, a three centimeter length of the control wire extends distal of the superior cap and is slideably disposed in the control wire lumen 65 of the balloon catheter shaft 61.

As shown in FIG. 8, bullet 100 is secured to the balloon catheter shaft 61 at a position distal the balloon distal stem 82 and proximal the aperture 94. The bullet is secured to the balloon catheter shaft by means of two retaining bumps 101 and 102 and alternatively in conjunction with adhesive. These retaining bumps secure the bullet in place, limiting its movement. Such a configuration provides a rounded, atraumatic transition from edge 103 of the superior capsule 93 resting on the top surface of the bullet when the superior capsule is at its most distal position as shown in FIG. 9.

As the control wire 91 is moved in a longitudinal manner, the distal end 95 of the control wire, the superior cap spacer 96, the superior cap 92, the superior capsule 93 and the nose cone 105 each move as a single assembly. The proximal edge 103 of the superior capsule is rolled, curved or crimped inward, or deburred and smoothened so that the bullet will provide a smooth transition along the superior capsule assembly 90 when the superior capsule is advanced. The distal movement of the superior capsule is limited by a third retaining bump 99 positioned approximately 2.5 centimeters distal the distal cap 92. The third retaining bump limits the amount of superior movement of the superior capsule assembly so that when the assembly is fully advanced the proximal edge of the superior capsule coincides with the top surface of the bullet 100.

The superior cap 92 may be formed from polycarbonate or other suitable material for insertion through the body lumen. Similarly, the superior cap spacer 96 and nose cone 105 may be formed of the same material as the superior cap. The superior cap spacer and superior cap provide a bore 104 for receiving the balloon catheter shaft. The superior cap is further provided with a recess 106 or other means for receiving the superior end of the superior capsule 93. The distal capsule is preferably formed of stainless steel, but may be formed of other suitable biocompatible material, such as a nickel titanium. The superior cap recess 106 is angled to allow crimping of the superior capsule 93 to the superior cap 92.

The outside diameter of the superior cap 92 and capsule 93 may range from 4 to 9 millimeters and is preferably 0.282 inches (7.16 mm) in outer diameter and 0.276 inches (7.01 mm) inner diameter. Similarly, the bullet 100 is comprised of stainless steel and has an outside diameter slightly less that of the superior capsule so as to provide a smooth transition. The proximal end of the bullet is preferably rounded to minimize trauma in the vessel and to facilitate balloon retraction into the tapered graft 55 during the emplacement process. In an alternate embodiment, the bullet may have a tapered profile. The superior capsule may range in length from one to five centimeters, and preferably is 3.5 centimeters long so as to adequately retain the superior extremity of the main tubular member of the graft. The nose cone 105 may range from 1 to 5 centimeters and preferably is 3.8 centimeters long.

As shown in FIGS. 1 and 11, a handle assembly 110 is secured to the proximal end of the control wire 91. The handle assembly comprises a body 111, a control knob 113 with rotating shaft 114 and a hypotube 115. For ease of manufacturability and simplicity of design, the handle body has a one-piece design. Also, the body has a central bore 119 for receiving the balloon catheter shaft 61 as well as a retaining screw 118 for longitudinally locking the retaining rack relative to the handle.

The hypotube 115 is coaxially disposed over the balloon catheter shaft 61 and extends distally from the central bore 119 in the handle body 111. The proximal end of the hypotube is secured to the balloon catheter shaft by means of a polyethylene sealing tube 116 which is heat shrunk over the proximal end of the hypotube. An adhesive may be used to fix the distal handle body to the hypotube.

Hypotube 115 consists of a rigid thin wall tube formed of a suitable material such as stainless steel. The hypotube has a length of about 55 centimeters and has an outside diameter of 0.095 inches (2.41 mm) and an inside diameter of 0.087 inches (2.21 mm). The hypotube may have marker bands (not shown) at predetermined positions distal of the control handle body 112. A graft may be loaded into the capsule assemblies in its most stretched configuration. After the capsule jacket assembly 53 is retracted, then adjustments need to be made to the position of the hypotube relative to the capsule catheter assembly 52 for the graft to resume its crimped length under physiological pressure. The marker bands facilitate the correct positioning of the inferior end of the graft.

The control wire 91 (see FIGS. 4, 23) resides in a balloon catheter lumen 65 and extends from the superior capsule assembly 90 to an aperture 117 located in the lumen just proximal of the proximal end of the hypotube 115. The control wire may consist of an elongate solid flexible stainless steel wire having a lubricating coating, such as fluorinated ethylene-propylene (FEP). The coated control wire is about 0.02 inches (0.508 mm) in diameter, providing sufficient strength to move the superior capsule assembly without buckling or kinking.

The proximal end of the control wire 91 is secured to a retaining rack 120, which is approximately 4.5 centimeters long. The retaining rack is slideably disposed within the central bore in the handle 111 and is in coaxial alignment with the balloon catheter shaft 61 and control wire 91. This coaxial design provides precise control of the relative movement of the control wire (including the components attached thereto), and remaining portions of the aortoiliac intraluminal grafting system 50.

The retaining rack 120 is configured with teeth 123 along a longitudinal edge which engage a pinion or gear 124. The pinion is attached to a lower end of the rotating shaft 114. The upper end of the rotating shaft is secured within the control knob 113 such that rotation of the control knob rotates the gear and in turn moves the retaining rack, including the components attached thereto, longitudinally within the central bore 119. Longitudinal movement of the retaining rack causes longitudinal movement of the proximal end of the control wire 91, causing like longitudinal movement of the distal end 95 of the control wire and of the superior capsule 93 (including the components attached thereto). The base of the control knob 113 is configured with a locking gear 125 which has angled teeth. The angled teeth engage a locking pin 126 which can be biased by a locking spring (not shown). The configuration of the curved teeth allows the control knob to turn in only one direction while the locking pin engages the locking gear. When the locking pin is removed from engagement with the locking gear 125, then the control knob may be turned in either direction. The locking gear is preferably molded as part of a plastic control knob, but may be a separate mechanism secured to the base of the control knob.

As shown in FIGS. 1, 5, 12 and 13, the inferior capsule catheter assembly 52 consists of a proximal or inferior capsule catheter assembly 130 secured to the distal end of a flexible elongate tubular member 131 formed of a suitable plastic material such as polyether block amide available under the trademark "PEBAX", available from Atochem Polymers, Glen Rock, N.J. The capsule catheter elongate tubular member is of a suitable length as, for example, forty to one hundred centimeters and preferably approximately seventy-five centimeters for the abdominal aortic-iliac arteries. The elongate tubular member has a preferred outside diameter of 0.187 inches (4.75 mm) and an inside diameter of 0.125 inches (3.175 mm). The elongate tubular member can be produced in a certain color such as blue. Preferably, the elongate tubular member can be extruded with braided wire to improve torsional response. To render the elongate tubular member radiopaque under x-rays, its material of construction may contain a radiopaque material, such as twenty percent by weight of bismuth subcarbonate or barium sulfate. The elongate tubular member may have markings or bands distal of the handle 145 at predetermined positions to indicate capsule jacket retraction and locking points.

The inferior catheter assembly 130 includes an inferior capsule 132 mounted on the distal extremity of the capsule catheter elongate tubular member 131. The elongate tubular member also serves as a shaft for advancing the inferior capsule, as hereinafter described. Thus, the elongate tubular member should have a diameter which is less than that of the inferior capsule, preferably having an outside diameter ranging from three to seven millimeters.

The inferior capsule 132 is configured to approximately match the size of the superior capsule assembly 90. The inferior capsule has a round cross-sectional profile (FIG. 25). The inferior capsule has a preferred diameter ranging from four to nine millimeters, which may be configured to accommodate different size grafts. The inferior capsule is preferably made of stainless steel or similar impermeable and rigid, or semi-flexible material.

Referring to FIG. 8, the inferior capsule 132 is secured to the distal extremity of the elongate tubular member 131 by means of a capsule adapter assembly 133. The capsule adapter assembly comprises a housing 134, which may be constructed from polycarbonate. The capsule adapter housing distal extremity 136 is secured in the proximal extremity of the capsule, for example, by crimping, by using a press fit swaging or an adhesive such as a cyanoacrylate ester. The capsule adapter housing distal extremity may be angled to facilitate securing the housing to the inferior capsule.

The proximal extremity of the capsule adapter housing 134 is secured to the distal extremity of the elongate tubular member 131 by means of an cyanoacrylate ester adhesive, or other suitable means. To facilitate a mechanical lock, the elongate tubular member distal extremity is molded to form a flange 137, wherein the capsule adapter housing is configured so as to mate with the flange. Preferably, the capsule adapter is of polycarbonate material insert molded to the distal extremity of the elongate tubular member 131.

As shown in FIGS. 1, 12 and 13, an inferior or proximal capsule handle 145 is secured to the proximal extremity of the elongate tubular member 131 of the inferior capsule catheter assembly 52. The inferior capsule handle comprises, for ease of manufacturing and simplicity in design, a one-piece body 146, a control knob 147 with rotating shaft 148 and a swing lock assembly 158 which tightens around the hypotube 115 disposed in a central bore 159 of the handle. The central bore 159 also receives the elongate tubular member 131 of the capsule catheter assembly. A stop cock 149 is mounted on the tubular member 188 extending from retaining rack 192 within the one-piece body 146 and being in fluid communication with the elongate tubular member 131 therein which is movable between open and closed positions. The stop cock is provided with a Luer fitting 150 which is configured to accept a syringe for injecting a dye or other fluid. Air may be purged from the capsule jacket assembly 53 by injecting fluid through the Luer fitting 150. The injection fluid and air will exit purge ports 151 and 152, thereby filling the capsule jacket assembly with injection fluid. The Luer fitting also may be attached to a saline drip line during the operative procedure and may be used for contrast hand syringe injections for real time angiograms.

The locking wire 85 is disposed in the inferior capsule catheter assembly 52 through a slotted opening 184 in the swing lock assembly 158. The swing lock assembly includes a rotating arm 186, shaft 187 and opposing members 188. The slotted opening is formed in one of the two opposing members. Additionally, opposing members provide a throughway for the balloon catheter shaft 61 contained within hypotube 115. Upon activation of rotating arm 186, the balloon catheter shaft can be locked and unlocked via the hypotube 115.

Slideably disposed within central bore 159 is a retaining rack 192 which is in coaxial alignment with elongate tubular member 131. Also disposed within the central bore is a spring 233 which operates to bias the retaining rack distally and to support the lock wire when subjected to compressive loads during the deployment of the ipsilateral attachment system prevent ing wire buckling, kinking or bowing. The proximal end of the elongate tubular member is secured to the retaining rack. The coaxial design of the rack and elongate tubular member provides precise control of the relative movement of the elongate tubular member, the components attached thereto, and the remaining portions of the intraluminal grafting system 50. The retaining rack is configured with teeth 201 along a longitudinal edge which engage a pinion or gear 224 fixed to the lower end of a shaft 227. The upper end of the shaft is secured to control knob 147 such that rotation of the central knob rotates the gear and in turn moves the retaining rack longitudinally within the central bore. Longitudinal movement of the rack causes longitudinal movement of the elongate tubular member and of the capsule 132 (including the components attached thereto). The control knob is configured with a locking gear 234 which has angled teeth for releasably engaging a locking pin 237. The locking pin can be biased by a locking spring (not shown).

Referring to FIGS. 1, 6 and 8, the capsule jacket assembly 53 is slideably disposed coaxially over the inferior capsule catheter assembly 52 and the balloon catheter assembly 51

(FIG. 24). The capsule jacket assembly is comprised of a main sheath 160, a locking assembly 162 which includes opposing members 164 and rotating arm 165. The sheath has a one piece design for ease of manufacturability and simplicity in design and is preferably made from HDPE or equivalent material such as LDPE, FEP, PET. At the distal extremity of the sheath, it flares to a larger diameter covering the proximal capsule 132, the contralateral capsule 202, the tapered graft 55 and the superior capsule 93. The diameter of the main sheath is about 0.263 inches (6.68 mm) at its proximal end and about 0.3 inches (7.62 mm) at the distal end 163.

The proximal end of the sheath 160 is secured to the locking assembly 162 by mechanical means and by adhesive. In addition, a length of polyethylene tubing 167 is adhered over the sheath adapter and over the proximal ends of the sheath to secure the parts from separating. The distal end of the sheath of the capsule jacket is provided with a radiopaque marker 166 about five millimeters in longitudinal length. The preferred embodiment is an "L" shaped marker of 3 mm LEG×5 mm LEG×2 mm WIDTH gold radiopaque foil laminated 2 mm from the distal extremity 163 of capsule jacket assembly 53.

When the capsule jacket assembly 53 is in its most distal position, the distal end 163 of the capsule jacket main sheath 160 extends to cover at least a portion of the superior capsule assembly 90. Similarly, the capsule jacket locking assembly 162 is thereby positioned just proximal the inferior capsule catheter purge port 151. Prior to insertion into the lumen, the rotating arm 165 is turned to lock the capsule jacket assembly firmly in place, thereby maintaining a smooth transition surface along the length of the aortoiliac intraluminal grafting system 50. When the locking ring/adapter is released, the capsule jacket assembly may be moved to a furthermost inferior position, wherein at least a portion of the inferior capsule catheter assembly is exposed. At its furthermost proximal position, the locking connector is positioned adjacent the distal of the inferior capsule handle 145. The distal end of the inferior capsule handle is configured with a male component 154 and mates with the proximal end of the locking connector. The locking ring/adapter may be tightened at any intermediate position to firmly secure the capsule jacket assembly at the desired location. In addition, a radiopaque marker 166 is provided at the distal end of the main sheath to facilitate proper linear positioning of the main sheath. As shown in FIGS. 7 and 14, the aortoiliac intraluminal grafting apparatus 50 also includes an expandable, collapsible and flexible intraluminal vascular tapered prosthesis or graft 55 for implanting in a body vessel or corporeal lumen. Referring to FIG. 14, the graft consists of a deformable main tubular member 170 which tapers down to a more narrow inferior tubular portion 171. The main tubular member and inferior tubular portion each are formed of a substantially cylindrical or continuous wall 173 allowing fluid communication between the superior and inferior ends of the tapered graft. The inferior tubular portion may be crimped so that kinking is resisted. Likewise, the main tubular member may be crimped (not shown). Where crimping is not desired, it may be omitted from the structure of the graft.

Although the graft 50 may have a number of various tapered configurations, in one preferred embodiment, the main tubular member 170 may have a length in the range of two to ten centimeters, where 6.5 centimeters is suitable for most patients. The main tubular member may have a maximum expandable diameter ranging from fourteen to forty millimeters and a minimum diameter in a collapsed condition of 0.175 to 0.3 inches (4.44–7.62 mm). The inferior tubular portion 171 may have a length in the range of one to fifteen centimeters, where ten centimeters is suitable for most patients. The graft wall 173 can be woven of any surgical implantable material such as polytetrafluroethylene or a polyester fiber made from polyethylene terephthalate (PET), such as "DACRON" (Type 56). One material found to be satisfactory is "DEBAKEY" soft woven "DACRON" vascular prosthesis (uncrimped) sold by C. R. Bard of Billerica, Mass. In order to prevent unraveling of the woven material at the ends, the ends can be melted with heat to provide a small melted bead of material on each end. Alternatively, the prosthesis may be of PTFE material, knitted polyester or any surgical implantable material. The tapered graft 55 may be a modified bifurcated graft with one leg removed and sewn shut by way of a seam 251 located near the junction between the main tubular member 170 and the inferior tubular portion 171.

The tapered graft 55 described provides significant flexibility in repairing a bifurcated body lumen. Where an aortic aneurysm is being repaired, there is often insufficient room downstream of the aneurysm prior to a bifurcation to implant the inferior end of the conventional tube grafts. The situation can be further complicated by a condition where one branch of the bifurcation is severely diseased and conventional bifurcation grafts cannot be used since there is nowhere for one leg of the bifurcated graft to be implanted. The tapered grafts 55 of the present invention can be used to repair such a body lumen because it is contemplated to be configured to extend past the wye of the bifurcation, thereby avoiding the problem associated with insufficient implant room near a bifurcation. Additionally, by lacking the two legs of a bifurcated graft, the tapered grafts can be implanted at the wye of a bifurcated body lumen even where one of its branches is severely diseased.

In a patient where one branch of a bifurcated body lumen is severely diseased, it being nearly entirely blocked by stenosis or greatly weakened due to an aneurysm, an occlusive device 260 (see FIG. 15) may be placed within the severely diseased branch and a tapered graft 55 without opening 251 placed at the wye with its inferior tubular portion 171 positioned within the other branch. Where such a condition occurs in the aortoiliac region of a patient, using standard surgical procedures, a femoral-femoral bypass is then made from the branch occluded by the occlusive device downstream of the occlusive device to its counterpart branch downstream of the inferior tubular portion of the tapered graft. It is understood that the occlusive device may be within other lumens which are not diseased for the purpose of temporarily or permanently occluding the lumen. It may be advantageous to do so, for example, to block unwanted flow during a surgical procedure.

The occlusive device 260 of the present invention embodies a windsock configuration. A first end 261 of the occlusive device defines its opening. A second end 262 can be completely closed or include a small opening 263 and an inverted graft tube section or flap 264 which closes in response to fluid pressure. Internal elongate tufts 272 made from dacron or equivalent material are located about an interior of the occlusive device. External tufts 273 are positioned about the outside of the occlusive device 260.

The preferred embodiment of the occlusive device is made from graft material. It can be tubular graft material that is sewn to provide a desired configuration or it can be fabricated into a desired shape without requiring sewing.

Preferably, the profile of the occlusive device is less than 19 French, with 14 French being the most common size. A wide range of diameters (8–16 mm) can be provided as well as lengths. It is anticipated that a length of 1–3.5 cm should be acceptable for most patients with the neck of the "windsock" being at least 1.2 cm. The small opening 263 has a diameter in the range of 1–3 mm and preferably 2 mm.

Figure 17:
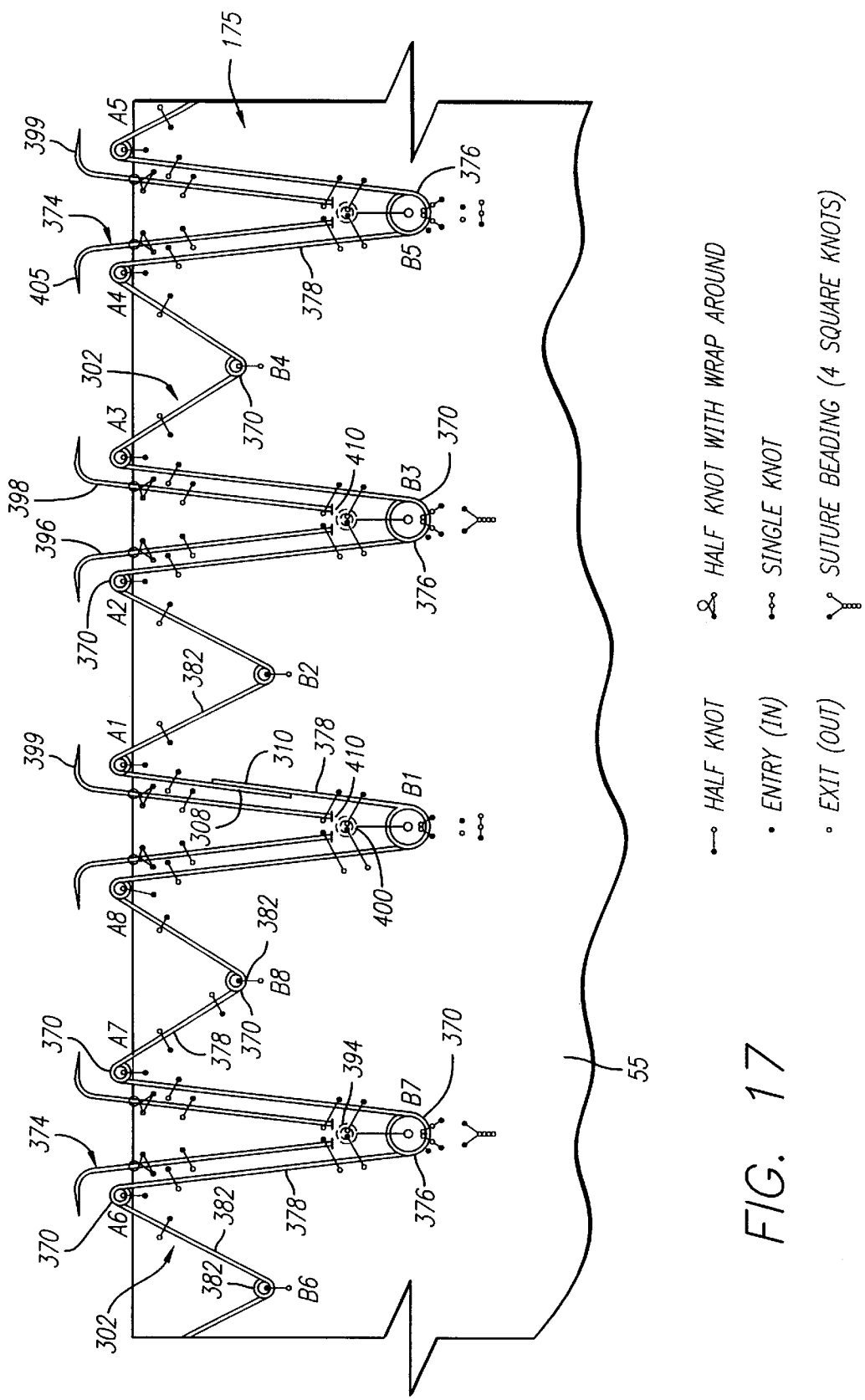
FIG. 17 is a plan view of the inside of the tapered graft cut longitudinally, showing a superior attachment system as sewn into the main tubular member of the graft.
Figure 18:
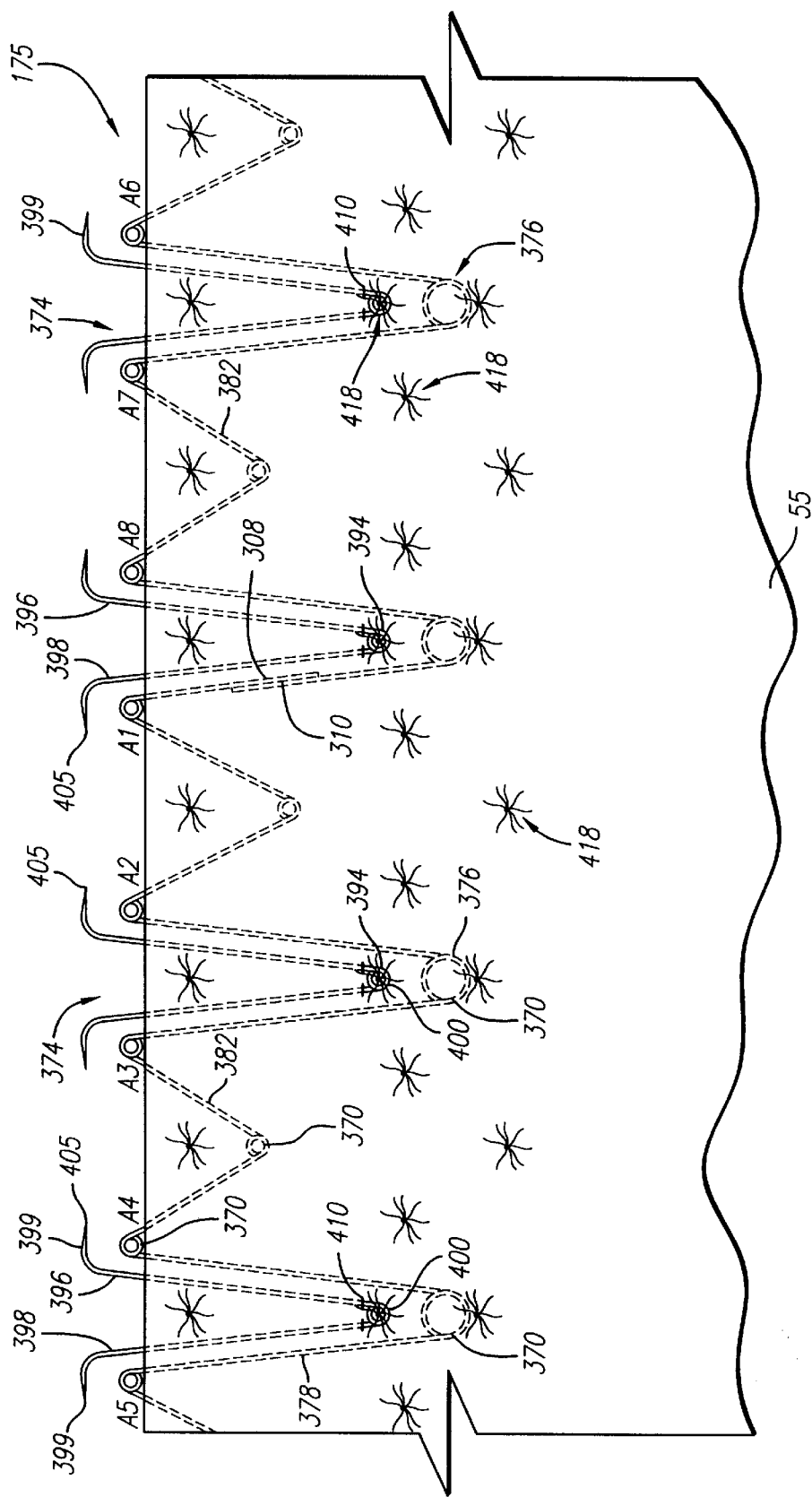
FIG. 18 is a plan view of the outside of the tapered graft cut longitudinally, showing in partial hidden view the superior attachment system wire frame and separate lumen engaging members and further showing the tufts attached to the graft.
Figure 19:
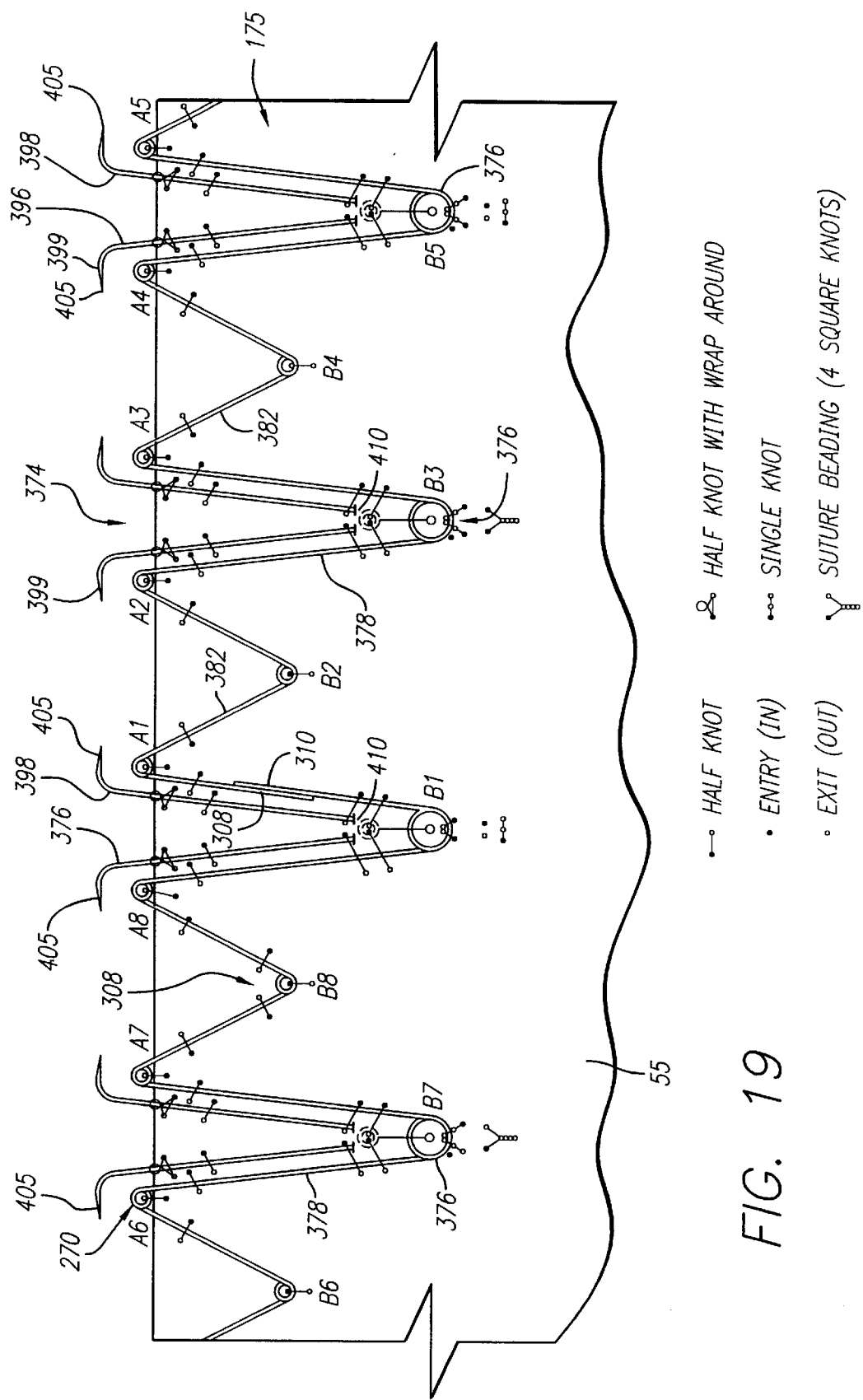
FIG. 19 is a plan view of the inside of the tapered graft cut longitudinally, showing an alternative embodiment of the wire frame, lumen penetrating members and stitching of the attachment system.
Figure 20:
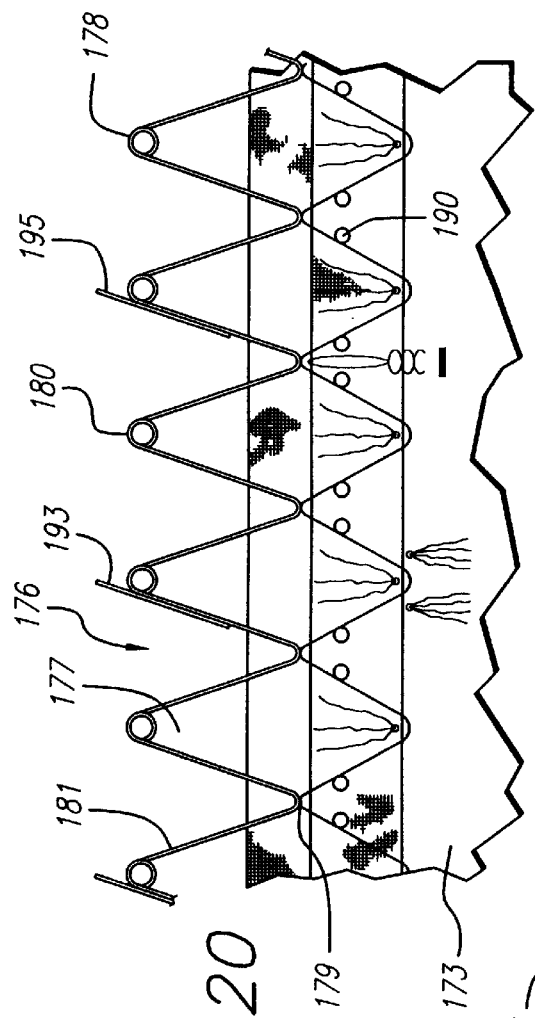
FIG. 20 is a top plan view showing an attachment system as sewn into an inferior end of the graft.

Referring to FIGS. 14, 15, 17–19, a self-expanding superior attachment system 175 is secured adjacent the superior end of the main tubular member 170. As shown in FIGS. 14 and 20, a self-expanding inferior attachment system 176 is secured adjacent the inferior end of the inferior tubular portion 171. Each attachment system serves to yieldably urge the tapered graft 55 from a first compressed or collapsed position to a second expanded position and provides a substantially fluid tight seal between the graft and corporeal lumen wall. As shown in FIGS. 17–19, the superior attachment system 175 includes a sinusoidal frame 302 that has longitudinally inwardly directed base apices that are affixed to the graft longitudinally inward from the outer extremity. Alternatively spaced between the sinusoidal frame are outwardly directed protruding apices that extend outward from the end of the graft. As shown in the embodiment illustrated in FIG. 17, the wire frame has a first end strut 308 and a second end strut 310. In the preferred embodiment, the first and second end struts of the single piece of wire frame are welded together to provide a continuous spring like attachment system. The wire frame is wound into helical coils or helices with one and a half rotations and include apices A1 through A8.

In the preferred embodiment, the sinusoidal wire frame 302 is formed with eight outward protruding apices numbered A1 through A8 respectively beginning at the protruding apex A1 closest to the first end. Each of the apices are wound into a helical spring coil 370. The alternating base apices are numbered for reference B1 through B8 beginning with the base apices closest to apex A1.

Each of the protruding apices A1 through A8 are integrally connected to adjacent base apices B1 through B8 by struts 378. As observed in FIG. 17, not all of the struts are of equal length. Rather, the length of the struts are configured to stagger the apices along different planes that are spaced longitudinally apart and are perpendicular to the axis of the graft 55 according to the pattern described below. It is an important objective of the present invention to create a narrow profile for the attachment system 175 when the attachment system is constricted radially. Since the helical apices tend to have a greater radial width than the struts, staggering the apices serves the purpose of creating a narrow profile for insertion into a capsule. The helixes 370 located at outward protruding apices A1 through A8 are aligned slightly outward from the end of the graft. Furthermore, the diameter of the helices 370 at aspice A1 through A8 are 0.042" inches which is smaller in diameter than helices 376 and 382. This accomplishes the purpose of minimizing the radial profile of the graft in collapsed position. The graft provides considerable bulk to the attachment system 175 and positioning the apices A1 through A8 beyond the end of the graft distributes longitudinally the bulk of the graft and helices.

The helixes 370 located at the base apices B1 through B8 are staggered considerably. Apices B1, B3, B5, and B7 are configured with slightly larger diameter helices 376 to accommodate the lumen piercing members 374 which are bent into the shape of a vee. V-shaped lumen piercing members 374 will fit between the struts 378 adjacent to apices B1, B3, B5 and B7 in a close proximal relationship. The lengthened struts that connect the apices are sufficiently long to orient the apices B1, B3, B5 and B7 0.550" inches longitudinally inward from the protruding apices. Furthermore, the diameter of the enlarged helices 376 at apices B1, B3, B5, B7 are 0.050 inches (1.2 mm), which is considerably larger than the diameter of remaining smaller helices 382 formed in the wire frame 302. The smaller helices 382 have a diameter of 0.047 inches (1.1 mm) at apices B2, B4, B6 and B8. The enlarged helices 376, in combination with the lengthened struts 378, create a space between the struts 378 that extend longitudinally outward from the enlarged helices 376 formed in apices B1, B3, B5 and B7 that conform in shape to the V-shaped lumen piercing members 374 such that the lumen piercing members can fit into the attachment system in close proximity to the lengthened struts and the enlarged helices, without contacting or rubbing against the same. As shown in FIG. 18 apices B2 and B6 may be further staggered with respect to apices B4 and B8. Apices B2 and B6 are oriented 0.46 inches longitudinally inward from the protruding apices. Apices B4 and B8 are oriented 0.36 inches longitudinally inward from the protruding apices.

As shown in FIG. 19, it may not be necessary or desirable under some circumstances to stagger apices B2 and B6 relative to B4 and B8. For example, the profile of the protruding apices A1 through A8 of the attachment system 175 might be sufficiently large that even if the staggering of helices B2 and B6 relative to B4 and B8 occurred it would not serve to reduce the diameter of the overall capsule. When staggering apices B2 and B6 relative to B4 and B8 would not serve to facilitate the use of a narrower capsule or delivery system, then aligning such apices may be desired.

The wire frame 302 of the attachment system 175 illustrated in FIGS. 17 through 19 is designed to fit inside a graft 55 that has a diameter of 20 to 26 millimeters but may range from 18 to 28 mm. The two ends of the wire frame, 308 and 310, overlap and are welded to each other.

The attachment system 175 including the wire frame 302 and the V-shaped lumen piercing members 374 are sutured to the tapered graft 55 at various points throughout the graft. The sewing pattern can best be viewed with reference to FIGS. 17 or 19 showing the stitching from the perspective of the inside of the graft.

In the embodiment illustrated in of FIGS. 14, 17–19, the V-shaped lumen piercing members 374 are not welded to the wire frame 302, but rather are sewn into the graft 55 in close proximity to the sinusoidal wire frame and are responsive to the compression and expansion of the wire frame. To provide stability and flexibility, the lumen piercing members are formed from a single strand of wire with two ends. The wire is bent into a V-shape having an apex 394 and two outwardly protruding arms 396 and 398 that form an acute angle when in relaxed position. The two ends of the wire are bent radially outward to form hooks 399 that, when mounted to the graft, are designed to pierce into the wall of the blood vessel. As shown in FIGS. 17–19, the hooks are shown to point tangential to the tapered graft perimeter. These illustrations are merely to show what the hooks look like. In actuality, the hooks would be directed at an angle perpendicular to the paper. At such an angle, the hooks would be difficult to illustrate. By incorporating this weldless design, the superior attachment system is better suited to withstand the loads or forces applied thereto when placed within a body lumen such as an aorta. Accordingly, being better suited for the environment in which it is placed allows the attachment system to more effectively anchor the graft within the lumen.

Each hook forms an angle with its respective arm ranging from ninety degrees to forty five degrees, but preferably seventy (70) degrees. The wire of each V-shaped lumen piercing member is wound at the apex to form a helical coil 400. Such a helical coil contributes to the outward bias and spring of the entire attachment system. Absent such a design feature, the V-shaped lumen piercing members would not be as responsive to the contractions of the graft. Moreover, the fatigue life of the hooks are extended because the helical design distributes the tension of the wire over the helix when the arms of the lumen piercing member are subject to continual contractions caused by the pulsing of the blood vessel during the cardiac cycle. The diameter of the apices in the embodiment illustrated in FIG. 17, 18 and 19 should have an outside diameter ranging between 0.025 inches and 0.060 inches and preferably 0.047 inches.

There are four pairs of V-shaped lumen piercing members 374 in the embodiment illustrated in FIGS. 17, 18 and 19. The number of V-shaped lumen piercing members mounted depends upon the number of pairs of protruding apices and base apices. The V-shaped lumen piercing members are placed around the graft equally spaced apart. They are fitted into the space between the elongated struts 378 and are mounted adjacent to apices B1, B3, B5, and B7. The arms of the Vshaped lumen piercing members extend parallel to adjacent elongated struts. The V-shaped lumen piercing members of the embodiment illustrated in FIG. 17 has a length of 13.5 mm and a helical diameter of 0.047 inches but may range from 10–20 mm.

The hooks 399 have a length of two to three millimeters and are sharpened at the tips 405. The hooks may be sharpened with a conical tip as shown in FIGS. 17 through 19 or with a duck billed tip (not shown). A conical tip is formed when the wire tip is held at an angle against the sharpening tool (not shown) and rotated. The duck bill tip is formed by holding one side of the tip of the hook 399 against the sharpening surface (not shown) at an angle. Not rotating the wire results in an oblong flat surface and a sharpened curved cutting edge that cuts into the blood vessel wall when the hook is pressed against the vessel wall.

One possible method of attaching the V-shaped lumen piercing members 374 to the frame can be observed with reference to FIGS. 17, 18 and 19. As can readily be observed, the helices of the V-shaped lumen piercing members are located on the outside of the graft 55 while the arms 396 and 398 extend parallel to the struts along the inside of the graft 55. The frame is positioned within the interior of the graft wall apexes A1–A8 extending just beyond the end of the graft. By mounting the V-shaped lumen piercing members directly through the fabric of the graft, the V-shaped lumen piercing members will be mounted more firmly. Furthermore, the fabric of the graft separates the helix 400 of the V-shaped lumen piercing member from the respective adjacent enlarged helices 376 and thereby prevents the helices of the V-shaped lumen piercing member from rubbing against the adjacent base helices.

The V-shaped lumen piercing members 374 are mounted into the tapered graft by pressing together the two arms 396 and 398 of the V-shaped lumen piercing members until the hooks are separated by a distance approximately equal to the outer diameter of the helices. The hooks are then punctured through the fibers of the graft from the outside of the graft wall to the inside of the graft. The entry holes made by the V-shaped lumen piercing members are spaced longitudinally outward by more than the outer diameter of the helices 400 of the V-shaped lumen piercing members. The spacing apart of helices 400 of the V-shaped lumen piercing members prevents them from radially overlapping the enlarged base helices 376. This longitudinal spacing also furthers the goal of distributing the bulk of the attachment system thereby narrowing the radial profile of the graft when in a compressed state. The apices of the lumen piercing member, prior to insertion of the hooks through the graft, point outward towards the end of the graft. The two hooks should preferably be laterally aligned so that the entry holes 410 through the graft wall created by the hooks are laterally aligned. The V-shaped lumen piercing members are pressed through the puncture holes and slid inward along the arms until the helix 400 contacts the outer wall of the graft. The V-shaped lumen piercing members are inverted to an upright position thereby orienting the hooks radially outward to engage the wall of the blood vessel.

The arms 396, 398 of the V-shaped lumen piercing members 374 are compressed before being sewn to the graft 55 to maintain the outward bias of the graft. The distance between the arms at the edge of the graft is preferably four to six millimeters but may range from 3–8 millimeters. The arms are sutured to the graft parallel to and in close proximal relationship to the struts 378 adjacent to the Vshaped lumen piercing members. The arms of the V-shaped lumen piercing members are generally not sutured directly to the adjacent struts. The arms of the V-shaped lumen piercing members and the adjacent struts are sutured separately in order to prevent them from rubbing together.

Referring to FIGS. 14 and 20, the inferior attachment system 176 is formed of a plurality of vees 177 with the outer apices 178 and inner apices 179 of the vees being formed with helical torsion springs 180. The inferior attachment system may be comprised of apices numbering from four to twenty-four. The springs yieldably urge the legs of each of the vees outwardly at a direction approximately at right angles to the plane in which each of the vees lie. The inferior attachment system 176 has legs 181, each being of equal length.

As shown in more detail in FIG. 20, the inferior attachment system 176 is comprised of a single piece of wire which is formed to provide the vees 177 and also to define the helical torsion springs 180 between the legs 181. The two ends of the single piece of wire can be welded together to provide a continuous spring-like attachment system. In the construction shown in FIGS. 14 and 20, it can be seen that the attachment system has twelve apices lying in two longitudinally spaced-apart parallel planes which are spaced with respect to the longitudinal axis of the inferior tubular portion 171. Accordingly, the outer apices 178 residing external of the graft are spread-apart from the inner apices 179 residing within the graft lie in the same plane. The apices, however, can lie in three or four spaced-apart planes if the inner and outer apices are staggered. As can also be seen, the inferior attachment system includes three wall engaging members 193 which are welded to the legs, and spaced uniformly about the attachment systems.

The attachment system 176 may be sewn to the graft such that the inner apices 179 are positioned 2.5–3 centimeters within the interior of the graft. The inferior attachment system 176 is secured to the wall 173 of the tapered graft 55 by suitable means such as a polyester suture material. As shown in FIG. 20, sutures or knots 190 are used for sewing the inner apices 179 onto the wall of the inferior tubular portion 171.

Figure 21:
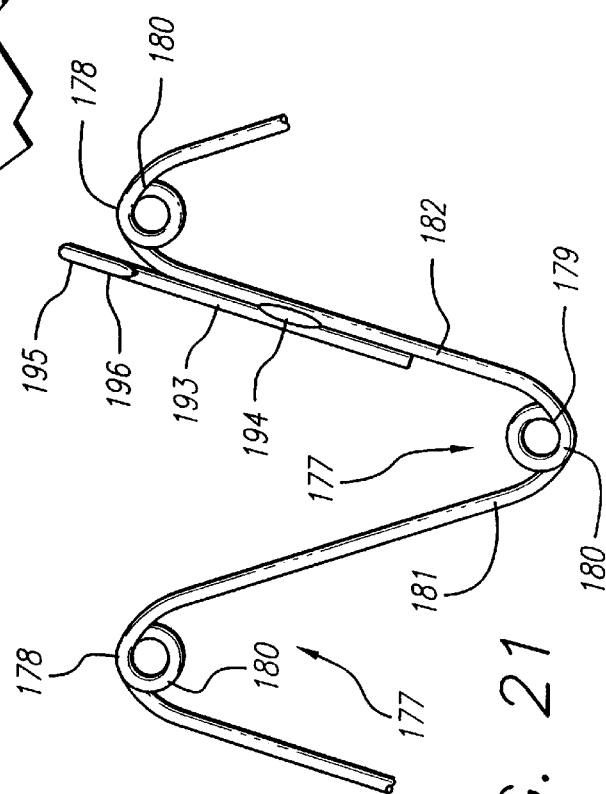
FIG. 21 is an enlarged side plan view showing an attachment system for the inferior end of the graft.

As shown in FIG. 21, wall engaging members 193 are preferably secured to the legs 181 of the inferior attachment system 176 in the vicinity of the outer apices 178 by suitable means such as a weld 194. The wall engaging members have a diameter ranging from 0.007 to 0.018 inches (0.254–0.457 mm) and a length from 0.5 to 5.0 millimeters. The wall engaging members are preferably sharpened to provide conical tips 196, and should have a length which is sufficient for the tip to penetrate into and perhaps through the corporeal lumen wall. The wall engaging members of the inferior attachment system 176 are configured in a similar manner. In the preferred embodiment, in order to provide additional structural support to the wall engaging members, the suture material used to sew the attachment system to the graft is wrapped around the legs of the attachment system to which the wall engaging members are welded, through the adjacent apices and is anchored to the graft.

The superior attachment system 175, inferior attachment system 176 and the wall engaging members 193, 374 are formed of a corrosion resistant material which has good spring and fatigue characteristics. One such material found to be particularly satisfactory is "ELGILOY" which is a cobalt-chromium-nickel alloy manufactured and sold by Elgiloy of Elgin, Ill. The wire can have a diameter ranging from 0.008 to 0.025" inches (0.203–0.406 mm), with a smaller diameter wire being utilized for the smaller diameter grafts. For example, 0.012 to 0.016 inch (0.305–0.406 mm) diameter wire for the frame and wall engaging members may be used in the larger grafts of eighteen to twenty-eight millimeters diameter, and 0.008 to 0.012 inch (0.203–0.305 mm) diameter wire may be used in the smaller grafts being eight to sixteen millimeters in diameter.

It has been found that the spring force created by the helical torsion springs at the apices is largely determined by the diameter of the wire. The greater the diameter of the wire, the greater the spring force applied. Also, the longer the distances are between the apices, the smaller the spring force that is applied to the legs. It therefore has been desirable to provide a spacing of approximately eighteen millimeters between the outer extremities of the legs of the superior attachment system 175. Similarly, a spacing of approximately ten millimeters between the outer extremities of the legs of the inferior attachment system 176 is preferable, although smaller or larger distances may be utilized.

Figure 22:
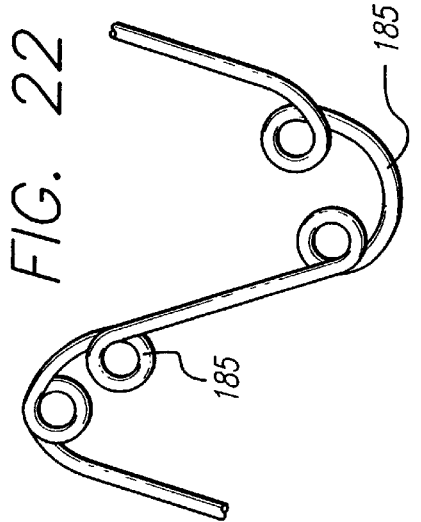
FIG. 22 is an enlarged side plan view showing an attachment system having a supplemental helix torsion spring at the apices.

FIG. 22 shows a low stress configuration of an attachment system. An additional helical torsion apex 185 is added along the legs of the attachment system. The additional apices are located adjacent the apices at the vees formed by the legs. Such a configuration improves the fatigue characteristics of the attachment system. In addition, the weld location for the welded attachment system may be moved down the attachment system leg to improve fatigue life. Alternatively, a non-round or non-circular wire, for example, a rectangular, conical or rounded ribbon wire, may be used to reduce the amount of stress in the attachment system and still maintain the spring force of the attachment system.

To facilitate securing the tapered graft 55 in the corporeal lumen, the tips 405 of the wall engaging members 374 on the superior attachment system 175 may be angled with respect to longitudinal axis of the main tubular member 170. The wall engaging member s face outwardly from the main tubular member to facilitate holding the graft in place. Preferably, the conical tips of the wall engaging members on the superior attachment system are inclined from the longitudinal axis and toward the inferior end of the graft by 55° to 90° and preferably about 85°. Likewise, the tips 195 of the wall engaging members 193 on the inferior attachment system 176 may be inclined towards the superior end of the graft by 30° to 90° and preferably 85°. By angling the conical tips of the wall engaging members so that they resist the force of the blood flow, the implanted wall engaging members oppose migration of the graft.

With respect to the occlusive device 260 (FIG. 15), either a superior-type attachment system 175 or an inferior-type attachment system 176 can be used to affix the occlusive device within a body lumen. The attachment system used to implant the occlusive device is placed at its opening and configured such that the wall engaging members project toward the walls of the lumen.

Where the occlusive device 260 is placed within a lumen wherein high pressures exist, a superior-type attachment system 265 is preferred. As the opening to the occlusive device is smaller than the opening to the superior end of the graft 55, the attachment system 265 for the occlusive device must be a smaller version of the superior attachment system 175. Preferably, the occlusive device attachment system has four inner apices 266 spaced 8–10 mm from outer apices 267 of which there are also four in number. Spaced between alternate apices are two v-hooks 268. The v-hooks 268 each include two diverging members 269, each having a length of 7–9 mm and terminating with a hook 270. The wall engaging members 268 are sharpened to provide a conical tip but may have other configurations.

The occlusive device attachment system frame and the v-hooks preferably have a diameter in the range of 8–16 mm and comprise the same material as the inferior or superior attachment system 175, 176. As with the superior and inferior attachment systems, each of the apices of the occlusive coil attachment system frame are preferably configured with helical coil springs 271.

Figure 16:
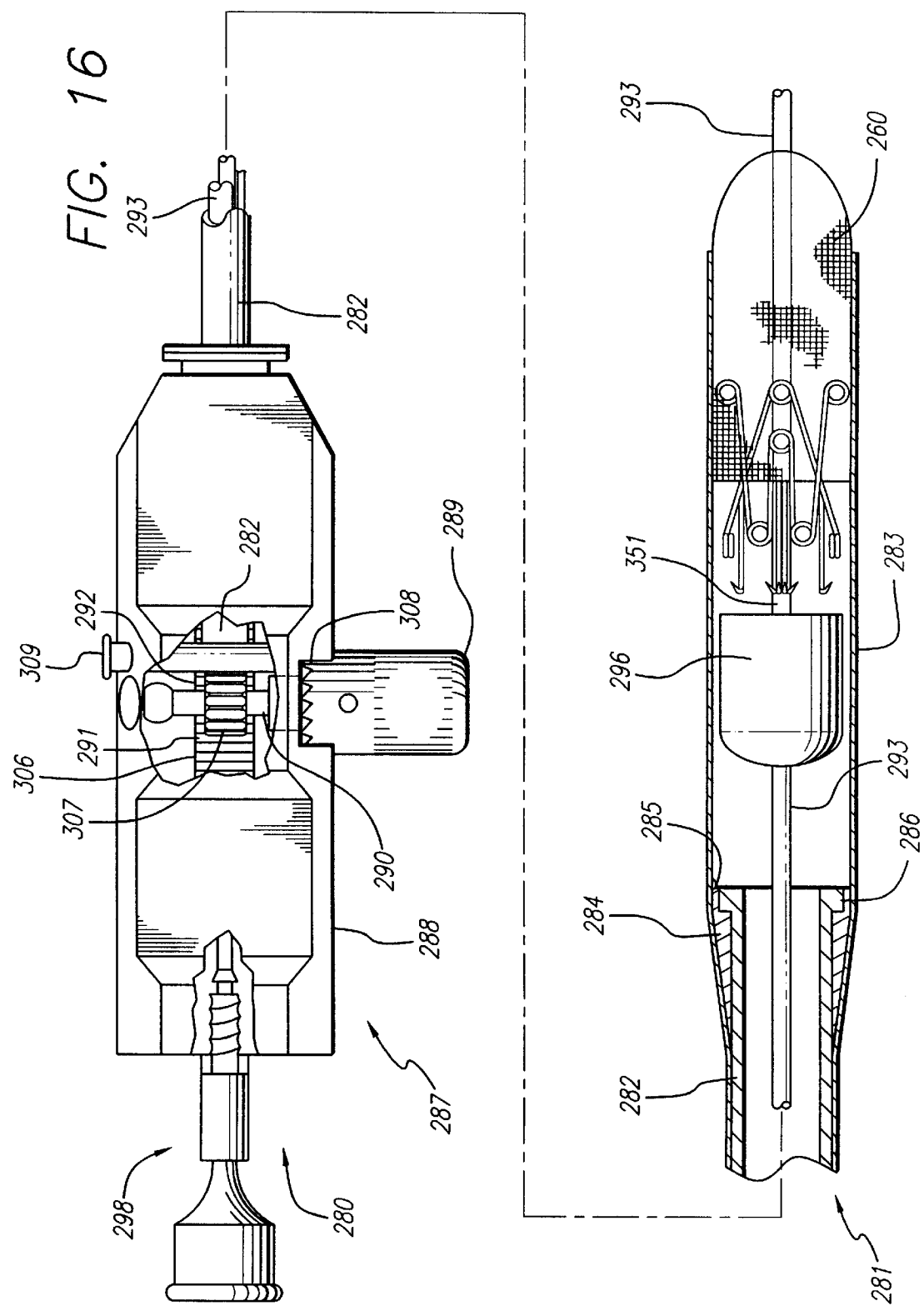
FIG. 16 is a partial cross-sectional view of a delivery system for the occlusive device, showing the occlusive device configured therein.

An occlusive device capsule catheter assembly 280 is provided to deliver the occlusive device 260 within a body lumen (FIG. 16). Like the inferior capsule assembly 52, FIG. 1 the occlusive device capsule catheter assembly consists of a capsule catheter assembly 281 secured to the distal end of a flexible elongate, single lumen tubular member 282. The capsule catheter assembly 281 includes a capsule 283 mounted on the distal extremity of the elongate tubular member 282 by means of an occlusive device capsule adapter assembly 283. The capsule adapter assembly includes a housing 284 which has a distal extremity 285 secured in the proximal extremity of the capsule. The proximal extremity of the adapter mates with a flange 286 formed on the elongate tubular member. The occlusive device catheter assembly comprises the same materials as the inferior capsule assembly and is assembled in a like manner. Its overall dimensions are 750–800 mm. The elongate tubular member has an inner diameter of 3.0–3.4 mm and an outer diameter of 4.7–5.0 mm.

An occlusive coil device capsule handle 287 is secured to the proximal extremity of the elongate tubular member 282. Like the inferior capsule handle 145, this capsule handle comprises a one-piece body 288, a control knob 289 with rotating shaft 290. The overall dimensions of the handle are 90–110 mm. A central bore 291 receives the elongate tubular member 282 of the capsule catheter assembly. The elongate tubular member is affixed to a retaining rack 292, which is configured to move longitudinally within the handle. A single lumen tubing 293 is configured slideably within elongate tubular member 284 and extends the length thereof. The proximal portion 294 of the single lumen tubing is fixed to the capsule handle 287. Its distal portion 295 is configured with a band 296 which is slideably retained within the capsule 283 and is adapted to engage the occlusive device and cause it to eject from within the capsule. When the capsule is retracted, the band is fixed relative to the handle.

The single lumen tubing has an inner diameter 0.8–0.9 mm and an outer diameter of 1.55–1.65 mm. Its proximal end portion is fixed to the capsule handle by means of an adaptor assembly 298 comprising a conventional barb adapter which mates with the single lumen tubing 293 at one end and a hex-head adapter at the other. The hex-head adapter is held against the capsule handle and is connected to a conventional luer adapter. The luer adapter is used to interconnect the hex-head adapter to a Toughy-Borst adapter.

The retaining rack 292 is slideably disposed within central bore 291 and is in coaxial alignment with elongate tubular member 282. Also disposed within the central bore is a spring 305 (not shown) which biases the retaining rack distally. The retaining rack is configured with teeth 306 along a longitudinal edge which engage a gear 307 fixed to the lower end of a shaft 290. The upper end of the shaft is secured to the control knob 289 such that rotation of the control knob rotates the gear and in turn moves the retaining rack longitudinally with the central bore, thereby causing longitudinal movement of the capsule 283 and the components attached thereto. The control knob is further configured with locking teeth 302 for releasably engaging a locking pin 309 which can be biased by a spring.

The helical torsion springs 180, 271, 370, 400 placed at the apices of the attachment systems serve to facilitate compression of the tapered graft 55 and occlusive device 260 in order to place attachment systems thereof within their respective capsule assemblies 90, 130 and 281, as hereinafter described. The compression of the graft and occlusive device is accomplished by deformation of the helical torsion springs to just outside their elastic limit, thereby having a small component within the plastic range. Placing the apices in different planes and staggering or offsetting the wall engaging members may significantly reduce the minimum compressed size of the graft. Having the wall engaging member in different planes also may help to prevent them from becoming entangled with each other. The natural spring forces of the helical torsion springs serve to expand the graft and occlusive device to their expanded position as soon as the attachment systems are free of the capsules.

The sizing of the tapered graft 55 and occlusive device 260 may be performed on a patient-by-patient basis, or a series of sizes may be manufactured to adapt to most patient needs. For the repair of an aortic aneurysm, the hook to hook length of the prosthesis is selected so to span the aneurysm, wherein the wall engaging members of the graft can seat within normal tissue of the vessel on both sides of the aneurysm. During the preimplant fluoroscopy procedure, a conventional pigtail angiography catheter is used to determine the locations of the renal arteries to ensure the renal arteries will not be covered by the implanted graft. Likewise, on the inferior end of the corporeal lumen, determining the location of the internal iliac arteries ensures that they will not be covered by the implanted graft. It is to be noted, however, that the internal iliac arteries are sometimes deliberately covered by the graft if there is adequate collateral circulation, as determined preoperatively by the physician. Also, the diameter of the main tubular member 170 and inferior tubular portion is selected by measuring the corporeal lumen which will receive the graft by conventional radiographic techniques. Similarly, the body lumen to be blocked by the occlusive device is measured to ensure a proper fit.

As shown in FIG. 14, segments or tufts of polyester yarn 418 or similar material may be sewn about the circumference of the graft 55. The segments or tufts 418 are used to produce a "fuzzy" thrombogenic surface to reduce blood leakage and improve blood clotting and coagulation along the superior end of the main tubular member 170. The filaments of the yarn segment are teased apart to increase the embolization area. The yarn segment is sutured to the wall 173 of the graft between the vees 177 of the superior attachment system 175.

Similarly, yarn segments may be attached to the graft wall adjacent the inferior attachment system 176. Alternatively, the graft may be made of velour or terry to similarly occlude blood flow through the ends of the graft adjacent the attachment system. Likewise, other modifications to the graft wall may be made to accomplish the same result.

FIG. 8 depicts the distal end of the aortoiliac intraluminal grafting system 50 assembled for deployment. The superior cap 92 is in its retracted or proximal position adjacent to bullet 100. Similarly, core wire 91 is locked via control knob 113 in its retracted or proximal position. During initial deployment, capsule catheter tubular member 131 is in its most distal position in relation to balloon catheter assembly 51 and is locked in place by the lever lock on the capsule catheter assembly.

The tapered graft 55 is disposed within the superior capsule 93, the inferior capsule 132, and the capsule jacket main sheath 160. The superior end of the main tubular member 170 and superior attachment system 175 are removably retained within the superior capsule 93. The inferior end of the inferior tubular portion 171 and inferior attachment system 176 are removably retained within the inferior capsule 132. During initial deployment, the distal end of the balloon catheter 80 is positioned such that the distal stem 82 of the balloon 60 resides within the main tubular member 170 of the graft 55, as shown in FIG. 8. The bullet 100 is positioned just proximal the superior cap 92 and is disposed within the superior capsule 93. In addition, proximal pusher button 86 and distal lock 87 are disposed on either side of the inferior attachment system 176 within the inferior capsule 132. In the preferred embodiment, distal pusher button 87 is disposed just distal the inferior attachment system 176. Also, the capsule jacket assembly 53 is longitudinally locked and positioned such that the distal end 163 of the capsule jacket main sheath 160 overlaps at least a portion of the superior capsule. During deployment, capsule jacket locking assembly 162 secures the main sheath in place. Thus, when any movement or force is applied to the handle assembly 145, the entire apparatus 50 moves as a single unit. It is also contemplated that the handle assemblies 145 and 110 have socket head shoulder screws 246 opposite the knobs for an elastic vessel loop (not shown). The loop mounted on the posts function as a counting element to the quantity and direction of rotations made between the two handles in the correction for graft twist between the main tubular member and the tubular legs.

By way of example, the following describes a method of repair of an aortic aneurysm located near a bifurcation using the method comprising the present invention for intraluminal placement of a tapered graft in an aorta. First, a patient is prepared in a conventional manner by use of a guidewire 56, a dilator and sheath (not shown) to access the ipsilateral femoral artery or vessel of the patient. In the preferred procedure, a super stiff 0.035" guidewire is used.

The distal end of the aortoiliac intraluminal grafting apparatus 50 is then inserted into the sheath over the super stiff 0.035" guidewire, which has previously been placed in the femoral artery. In the preferred embodiment of the present invention, balloon catheter lumen 63 is provided for receiving the guidewire 56 that was previously traversed across the aneurysm. However, the following procedure may also be used when the guiding member is constructed as part of the balloon catheter.

Next, the balloon catheter assembly 51, the inferior capsule catheter assembly 52, the capsule jacket assembly 53 and the control wire assembly 54 are all configured for deployment as shown in FIGS. 1 and 8. Thus, the assemblies may be advanced by the physician as a single unit over the main guidewire 56. As shown in FIG. 26, the main guidewire is introduced by the physician into an arteriotomy or introducer sheath in the ipsilateral femoral artery and advanced through the ipsilateral iliac artery 228 to the desired location in the abdominal aorta 225 and adjacent to the diseased or damaged portion 226 of the vessel.

The physician advances the distal end of the aortoiliac intraluminal grafting assembly 50, through the ipsilateral femoral artery over the guidewire 56, the nose cone 105 facilitating advancement about arduous turns. Typically, the desired position for implanting the tapered graft 55 will be within the abdominal aorta 225 with the superior extremity of the main tubular member 170 at least one millimeter inferior to the lower renal artery. The inferior attachment system 176 should be positioned superior the internal iliac artery. Alternatively, the interior attachment system may be deployed in the iliac below the internal iliac artery, but additional surgical intervention is necessary to provide blood flow into the internal iliac.

Thereafter, as shown in FIG. 27, the locking ring 165 of the capsule jacket assembly 53 is loosened to allow movement of the capsule jacket main sheath 160. While using one hand to firmly grasp the inferior capsule catheter assembly 52 and holding it stationary, the physician grasps the locking assembly 162 with the other hand and gently pulls it proximally towards the capsule catheter wye adapter. The capsule jacket assembly is gradually retracted to expose the superior capsule 93.

At this point in the procedure, as shown in FIG. 27, the superior end of the main tubular member 170, disposed in the superior capsule 93, is moved into the desired location of the aorta 225 by moving the control handle 145, and thereby the aortoiliac intraluminal grafting assembly 50, in a proximal direction. Concurrently, the inferior end of the inferior tubular portion 171, securely retained within the inferior capsule 132. In order to insure proper orientation of the tapered graft 55, the balloon catheter shaft lock can be disengaged and the superior capsule handle 110 rotated relative to the inferior capsule catheter assembly 52 to maximize the lateral radiopaque marking on the graft. Once these steps are performed, each of the attachment systems should be in position for deployment.

Figure 28:
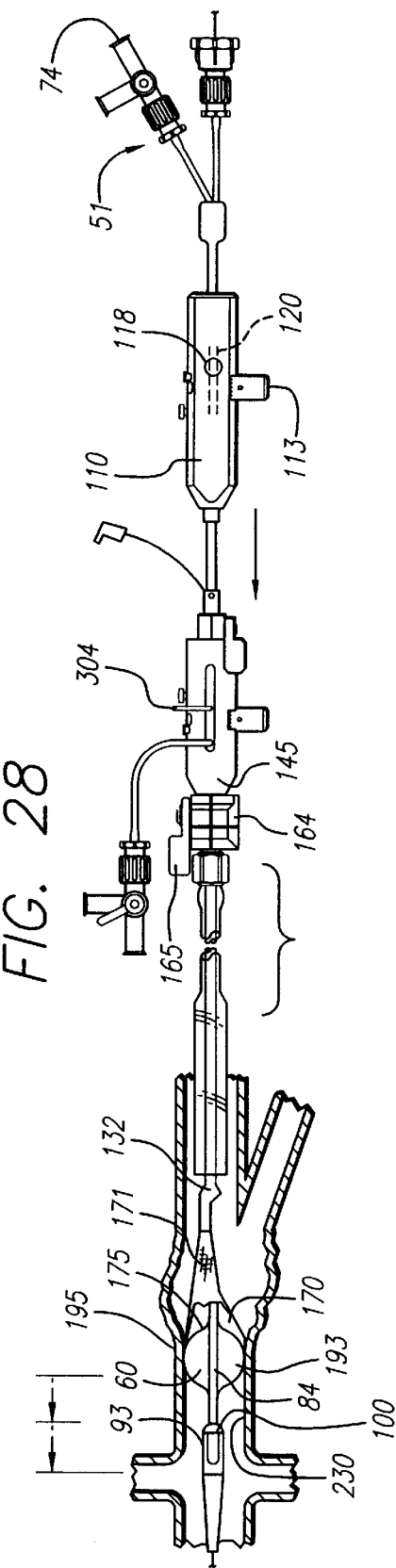
FIG. 28 is a partial cross-section view of the intraluminal grafting system, wherein the superior capsule has been removed from the superior end of the tapered graft and the inflatable member has been expanded to seat the superior attachment system.

The retaining screw 118 is loosened and the control knob 113 is then rotated to cause relative movement between the superior capsule assembly 90 and the balloon catheter assembly 51 to release the superior end of the main tubular member 170 and superior attachment system 175 from the superior capsule 93. Rotating the control knob causes the retaining rack 120 to move the control wire 91 in a distal direction. Since the superior cap 92, nose cone 105, and superior capsule 93 are secured to the control wire 91, and since the handle incorporates the coaxial design, they move in a precise manner and in corresponding relationship with the rotation of the control knob. As the superior capsule is moved from engagement with the superior attachment system, the balloon catheter bullet 100 locates at the proximal end of the superior capsule. The superior capsule is continued to be advanced so that a smooth profile of the superior capsule and the cap is achieved. As soon as the superior capsule has cleared the superior attachment system 175, the superior extremity of the main tubular member expands outwardly under the force of the self-expanding attachment system which springs into engagement with the vessel wall 230 (FIG. 28). The locking pin 126 holds the control knob, and thus the control wire and superior capsule, fixed in place.

Once the superior attachment system 175 is exposed, steps are taken to firmly seat or urge the wall engaging members 374 in the vessel wall. First, the swing lock assembly 158 on the inferior or proximal capsule handle is loosened to permit relative movement between the inferior capsule catheter assembly 52 and the balloon catheter assembly 51. While the physician uses one hand to hold the inferior capsule catheter assembly stationary, the handle assembly 110 is grasped by the other hand and pushed distally to position the center of the main balloon 60 into the superior extremity of the main tubular member 170 (FIG. 28). The radiopaque markers 84 are used to align the main balloon and superior attachment system. The balloon shaft 61 is then locked again by activation of the swing lock assembly.

Thereafter, a conventional hand operated syringe or inflation assembly (not shown) is attached to the balloon catheter inflation port 74. As depicted in FIG. 28, the main balloon 60 is then expanded by introducing a suitable gas such as carbon dioxide or a dilute radiopaque liquid from the syringe to urge the wall engaging members 193 outwardly to firmly emplace the superior conical tips 195 into the vessel wall 230. The main balloon may be deflated and inflated repeatedly to ensure the superior attachment system is firmly implanted in the vessel.

Additionally, the inferior capsule 132 and is then moved to its most proximal position and its proximal end 162 is locked to the male component 154 of the inferior capsule handle 145. When the proximal end is brought into contact with the male component 154, there is an audible click which signifies to the operator that the parts have been placed into engagement. The locking ring is then tightened to hold the capsule jacket assembly in place, as shown in FIG. 27. The radiopaque marker 166 at the distal end of the capsule jacket main sheath may be used to position the capsule jacket as desired.

The main balloon 60 normally remains in an inflated position during the next steps of the procedure. During the actual retraction of the inferior capsule 132, the main balloon should be inflated, further securing the superior attachment system 175. However, the main balloon may be deflated and reinflated during the following steps to allow the inferior tubular portion 171 to fill with blood to facilitate detecting any twisting of the tapered graft 55.

Figure 29:
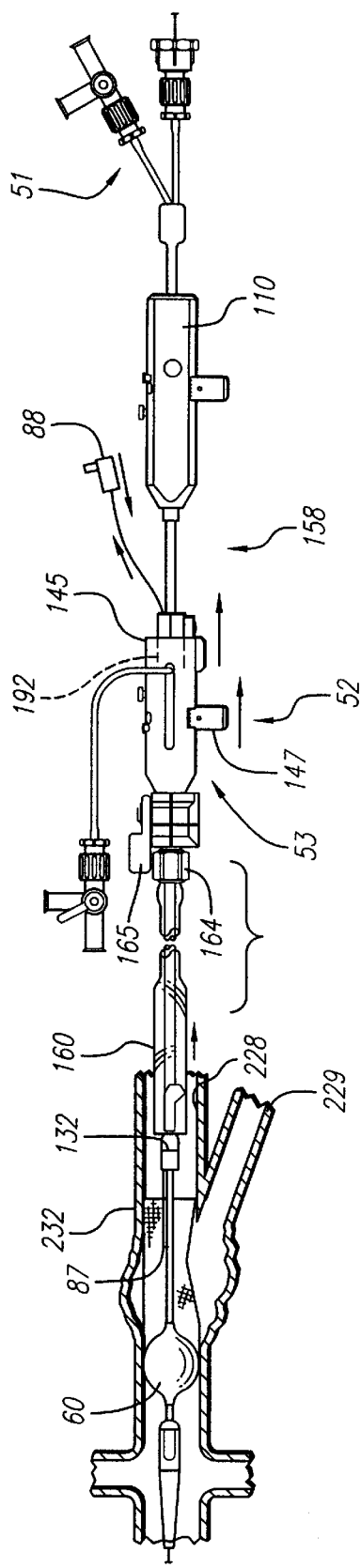
FIG. 29 is a partial cross-sectional view of the intraluminal grafting system, wherein the inferior capsule has been removed from the inferior end of the tapered graft, releasing the inferior attachment system into the ipsilateral iliac artery.

As shown in FIG. 29, the next step is to implant or anchor the inferior attachment system 176 of the inferior tubular portion 171 into the ipsilateral iliac artery 228. A retaining pin 304 configured to lock the proximal or inferior capsule handle 145 retaining rack 192 is then removed. The swing locking assembly 158 of the capsule handle 145 is locked to the balloon catheter. Then the control knob 147 is turned in order to effect longitudinal movement of the inferior capsule 132 and rack 192, precise control of which is achieved by way of the coaxial design of the handle. The inferior tubular portion 171 can be affixed within the vessel either in compression or tension. To deploy in compression, the pusher button 86 and lock 87 remain locked longitudinally to the handle 145. The handle assembly 110 is also longitudinally locked to the handle 145 with the balloon 60 inflated to secure the superior attachment system, while the capsule catheter rack 192 is moved proximally when the knob 147 is rotated until the inferior attachment system and inferior end of the inferior tubular portion are completely clear of the inferior capsule 132 while its position is held fixed relative to the corporeal lumen. To deploy the inferior portion in tension, both the ipsilateral locking wire 87 and pusher button 86 and the capsule catheter assembly 52 are moved proximally until the inferior portion 171 is held in tension. Thereafter, the capsule catheter assembly is moved further proximally while keeping the lock and pusher button stationary.

Whether deploying the inferior tubular portion 171 in compression or in tension, once the inferior extremity of the limb is free of the inferior capsule 132, the inferior attachment system 176 will spring open and the wall engaging members 193 will engage the ipsilateral iliac vessel wall 232. Leaving the main balloon 60 inflated while the inferior capsule catheter assembly 52 is moved ensures that the superior attachment system 175 will remain firmly secured in place. Thereafter, the main balloon 60 is deflated. The locking wire handle 88 is rotated 90° and retracted to release engagement with the inferior handle 145 to position the lock 87 and pusher button 86 back within the inferior capsule 132 for a smooth transition. As shown in FIG. 30, the handle assembly 110 is moved proximally so that the main balloon is retracted into the inferior tubular portion 171 and placed adjacent the inferior attachment system 176. If the main balloon cannot be positioned adjacent to the attachment system due to limited available movement of the handle assembly, then the swing lock assembly 158 is secured to the hypotube 115, thereby securing the inferior capsule catheter assembly to the balloon catheter assembly 51. The entire deployment catheter 50 is then moved proximally to position the main balloon adjacent the inferior attachment system.

The main balloon 60 may be inflated and deflated through the entire length of the main tubular member 170 and inferior tubular portion 171 to ensure patency of the tapered graft 55. Again, the balloon radiopaque markers 84 are used to align the center of the main balloon with the inferior attachment system 176. The balloon is then inflated just enough to expand the inferior attachment system to tack down the wall engaging members 193 into the ipsilateral iliac artery vessel wall 232. Thereafter, the main balloon is finally deflated.

As shown in FIG. 31, the inferior capsule assembly 130 and balloon 60 are moved proximal the tapered graft 55 and within the capsule jacket assembly 53. First the swing lock assembly 158 is loosened. Then, while holding the inferior capsule catheter assembly 52 in place by grasping the handle 145 with one hand, the balloon catheter assembly 51 is moved proximally by gently pulling the handle assembly 110 with the other hand. Thus, the capsule catheter assembly and balloon catheter are in the same relative position as they were just prior to deployment (FIG. 8). Also, the proximal end 103 of the superior capsule 93 has been mated with the bullet 100 for smooth transition.

Finally, the capsule jacket locking ring 165 is loosened and the proximal end of the capsule catheter is disengaged from the male member 154 and the distal end of the inferior capsule handle 145. While holding the capsule jacket locking assembly 162 in place, the balloon catheter assembly 51 and capsule catheter assembly 52 are moved proximally and in unison by gently pulling the handle 145 of the inferior capsule catheter assembly. The catheter assemblies are moved until the distal end 163 of the capsule jacket main sheath 160 covers the bullet 100 or until the inferior capsule adapter housing 134 mates with the flared transition of the capsule jacket, thereby creating a smooth transition along the entire length of the aortoiliac intraluminal grafting apparatus 50. Thereafter, the balloon catheter assembly, inferior capsule catheter assembly, capsule jacket assembly 53 and control wire assembly 54 are removed from the aorta through the femoral artery. The tapered graft 55 and attachment systems 175 and 176 remain secured to the vessel walls 230, 231 and 232, thereby sealing the aneurysm 226 from blood flow.

When the intraluminal grafting apparatus 50 is removed from the ipsilateral iliac and femoral arteries, the main guidewire 56 remains in place in the vessels. A conventional (ipsilateral) auxiliary balloon catheter (not shown) may be traversed over the main guidewire and positioned at the inferior end of the inferior tubular portion 171 and within the ipsilateral attachment system 176. An ipsilateral auxiliary balloon on the ipsilateral auxiliary balloon catheter may be inflated to firmly implant the conical tips 196 of the wall engaging members 193 into the ipsilateral iliac artery wall 232. The ipsilateral auxiliary balloon may be inflated and deflated along the entire inferior tubular portion to ensure the leg is completely open and to remove creases which may have set while the tapered graft was loaded in the capsule jacket assembly. Thereafter, the ipsilateral auxiliary balloon catheter is removed. The main guidewire is removed from the ipsilateral femoral artery after a post implant angiogram, introducer sheaths are removed and the cutdowns are closed after contra occlusion.

Where the contralateral branch of the bifurcation is severely diseased, steps are taken to deploy the occlusive device in the contralateral branch of the bifurcation. Alternatively, the occlusive device can be used independently of the aortoiliac grafting system 50 and placed within any body lumen for the purpose of occluding that lumen.

In order to deploy the occlusive device 260 within a body lumen, the occlusive device is configured within the occlusive device capsule assembly 280, as shown in FIG. 16. The occlusive device 260 is held within the capsule 283 by friction.

By way of example, the following describes a method of deploying the occlusive device 260 within a lumen using the occlusive device delivery system. First, the patient is prepared in the conventional manner by making a cutdown to gain access to the body lumen in which the occlusive device 260 is to be placed. Where the body lumen is the contralateral femoral artery, access is gained thereto and a dilator and sheath (not shown) is placed therein. A guidewire 56 like the one used to deploy the tapered graft 55 is then introduced into the patient's vasculature and advanced beyond the site at which the occlusive device is to be placed.

The band 296 configured on the end of single lumen tubing 293 of the occlusive device capsule catheter 280 is provided with a through hole 351 which is in fluid communication with the interior of single lumen tubing 293. The distal end 352 is then inserted into the sheath over the guidewire and into the patient's vasculature.

The physician advances the distal end 352 of the occlusive device capsule catheter 280 through the contralateral femoral artery and to the point at which the occlusive device 260 is to be deployed (FIG. 32). Next, holding the handle 287 of the capsule catheter stationary, the control knob 289 is rotated which causes the occlusive device capsule 283 to move proximally and relative to the band 296 which is held stationary in the vessel through its connection to the handle.

As the capsule moves proximally, the occlusive device is ejected from within the capsule (FIG. 33).

Once the occlusive device 260 is completely ejected from the capsule 283, its attachment system 265 springs open and the wall engaging members 270 become affixed to the walls of the vessel (FIG. 34). The occlusive device capsule catheter 280 is then withdrawn from the patient's vasculature. Should it be determined that it is necessary, a balloon catheter 51 like the one used in connection with the aortoiliac grafting system, is inserted in the body lumen over the guidewire and configured within the attachment system 265 of the occlusive device and expanded to fully seat the wall engaging members 270 within the walls of the lumen. The balloon catheter can be repeatedly expanded to ensure that the occlusive device is securely anchored. The balloon catheter is then removed from the patient's vasculature, the guidewire and sheath indentures removed and the cutdown closed.

Finally, where the occlusive device has been used in combination with the tapered graft to repair the aorto at the femoral bifurcation, conventional surgical techniques, a fem-fem bypass is performed (FIG. 35). The bypass functions to supply blood from the ipsilateral branch of the bifurcation where the tapered graft is placed to the contralateral branch caudally from the occluded region of the contralateral artery. It is to be noted that occlusion can be accomplished either by means of the occlusive device or some other means (i.e., ligation).

The entire procedure described herein can be observed under fluoroscopy. The relative positioning of the tapered graft 55, the occlusive device 260 and the balloon 60 can be readily ascertained by the radiopaque attachment systems 175 and 176, the radiopaque locking mechanisms 87, radiopaque markers 255, 256, 257 provided on the tapered graft, the radiopaque markers 84 on the balloon shaft 61 and the bullet 100. If any twisting of the graft has occurred between placement of the superior attachment system and the inferior attachment system, then the twisting can be readily ascertained by observing the series of graft markers. Adjustments to eliminate any twisting which may have occurred can be made before exposing the attachment systems by rotation of the balloon catheter 51 or the inferior capsule catheter assembly 52. Any excessive graft compression can be ascertained by observing the radiopaque markers under fluoroscopy. Adjustments to eliminate tapered graft compression can be made before exposing the inferior extremity of the graft by applying tension on the inferior capsule catheter assembly.

Additional attachment systems may be placed within the graft for the purpose of preventing kinking of the graft material. These additional attachment systems are placed medial the ends of the graft. Such medial attachment systems may resemble the inferior or superior attachment systems, but the medial attachment system are preferably configured without wall engaging members. The medial attachment systems are deployed using an auxiliary capsule catheter traversed over the main guidewire 56 or another guidewire inserted in the graft after the inferior attachment system 176 is firmly seated.

Post implant fluoroscopy procedures can be utilized to confirm the proper implantation of the device by the use of a conventional pigtail catheter or by injecting dye into the guidewire lumen of the balloon catheter shaft. Tissues should begin to grow into the graft and occlusive device within two to four weeks with tissue completely covering the interior sides thereof within six months. While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Accordingly, it is not intended that the invention be limited, except as by the appended claims.

What is claimed is:

1. A system for repair of a main corporeal lumen having a first corporeal lumen and a second corporeal lumen branching therefrom, comprising:

a graft, said graft having a tubular configuration with a superior end and an inferior end, the graft tapered from a larger diameter at its superior end to a smaller diameter at its inferior end and including at least one V-shaped member having legs terminating in hooked ends;

a graft delivery system, said graft delivery system adapted to intraluminally deploy said superior end of the graft within the corporeal lumen at a repair site within the main corporeal lumen and said inferior end in the first corporeal lumen;

an occlusive device configured to remain permanently within the second corporeal lumen, said occlusive device having a first and second end, said first end including a closeable opening, said second end defined by an opening providing access to an interior of said occlusive device; and an occlusive device delivery system, said occlusive device delivery system adapted to intraluminally deploy said occlusive device at a site in the second corporeal lumen.

2. The system of claim 1, wherein the system is configured to deploy said graft and said occlusive device near a bifurcation in the corporeal lumen, said graft placed in a main branch feeding a plurality of branches and extending into one of said branches, said occlusive device placed in another of said branches.

3. The system of claim 1, said graft delivery system further comprising:

an inferior capsule assembly; and a superior capsule assembly;

wherein said inferior capsule assembly releasably retains an inferior end of said graft and said superior capsule assembly releasably retains a superior end of said graft, said inferior and superior capsule assemblies being configured to move longitudinally relative to said graft in order to permit said graft to be deployed within the corporeal lumen.

4. The system of claim 3, said inferior capsule assembly being attached to a handle by an elongate tubular member, said handle including a rotatable knob, the rotation of which causes said inferior capsule to move longitudinally with respect to said handle.

5. The system of claim 3, said superior capsule assembly being attached to a handle by an elongate member, said handle including a rotatable knob, the rotation of which causes said superior capsule to move longitudinally with respect to said handle.

6. The system of claim 1, said graft further including an expandable superior attachment system attached to a superior end of said graft, said superior attachment system including a generally sinusoidal frame, said V-shaped members being interspaced between struts defining said frame.

7. The system of claim 1, said graft further including an expandable inferior attachment system attached to an inferior end of said graft, said inferior attachment system including a generally sinusoidal frame with a plurality of hook wall engaging members attached to struts forming said frame.

8. The system of claim 1, said graft delivery system further comprising:
 a balloon catheter assembly; and
 a capsule jacket assembly;
 wherein said capsule jacket assembly is configured to cover said graft during advancement of said graft within the corporeal lumen and to move longitudinally with respect to said graft in order to permit deployment of said graft within the corporeal lumen and said balloon catheter assembly is configured coaxially within said capsule jacket assembly and adapted to engage said graft in order to seat said graft within the lumen.

9. The system of claim 1, said occlusive delivery device further comprising an occlusive device capsule assembly, said occlusive device capsule assembly configured to releasably retain said occlusive device.

10. The system of claim 9, said occlusive device delivery system further comprising a tubular member extending proximally from said occlusive device capsule assembly, said tubular member attached to a handle, said handle including a rotatable knob, the rotation of which causes said capsule assembly to move longitudinally with respect to said occlusive device.

11. The system of claim 1, said occlusive device further comprising an inverted tube which is configured at an opening formed in said first end.

12. The system of claim 1, said occlusive device further comprising an expandable attachment system attached to said second end, said attachment system including a generally sinusoidal frame and a plurality of V-shaped members with hooked terminal ends, said V-shaped members being interspaced between struts defining said frame.

13. A graft for repairing a corporeal lumen, comprising:
 a main tubular body extending from a superior end of said graft;
 an inferior tubular portion extending from said main tubular portion of the body and defining said inferior end of said graft;
 said graft having a diameter which tapers from said main tubular body to said inferior tubular portion; and
 a superior attachment system secured to said superior end, said superior attachment system including a generally sinusoidal frame and V-shaped members interspaced between struts defining said frame.

14. The graft of claim 13, further comprising an inferior attachment system secured to said inferior end of said graft, said inferior attachment system including a generally sinusoidal frame and wall engaging members individually attached to struts defining said frame.

15. The graft of claim 13, wherein said V-shaped members include an apex, said apex further including a helical coil.

16. The graft of claim 13, said V-shaped members further including hooks formed at terminal ends thereof, said hooks being directed radially outwardly.

17. A system for repair of a corporeal lumen, comprising:
 a graft including at least one V-shaped member having legs terminating in hooked ends;
 a graft delivery system including a capsule assembly arrangement for releasably receiving said graft;
 an occlusive device, said occlusive device having a first and a second end, said second end defined by an opening providing access to an interior of said occlusive device; and
 an occlusive device delivery system, said occlusive device delivery system adapted to intraluminally deploy said occlusive device at the repair site.

18. The system of claim 17, wherein said graft has a main tubular body extending from a superior end and an inferior tubular portion extending from said main tubular body and defining an inferior end, said graft having a diameter which tapers from said main tubular body to said inferior tubular portion.

19. The system of claim 17, wherein the system is configured to deploy said graft and said occlusive device near a bifurcation in the corporeal lumen, said graft placed in a main branch feeding a plurality of branches and extending into one of said branches, said occlusive device placed in another of said branches.

20. The system of claim 17, wherein said capsule assembly arrangement includes:
 an inferior capsule assembly; and
 a superior capsule assembly;
 wherein said inferior capsule assembly releasably retains an inferior end of said graft and said superior capsule assembly releasably retains a superior end of said graft.

21. The system of claim 20, said inferior capsule assembly being attached to a handle by an elongate tubular member, said handle including a rotatable knob, the rotation of which causes said inferior capsule to move longitudinally with respect to said handle.

22. The system of claim 20, said superior capsule assembly being attached to a handle by an elongate member, said handle including a rotatable knob, the rotation of which causes said superior capsule to move longitudinally with respect to said handle.

23. The system of claim 17, said graft further including an expandable superior attachment system attached to a superior end of said graft, said superior attachment system including a plurality of wall engaging members.

24. The system of claim 17, said graft further including an expandable inferior attachment system attached to an inferior end of said graft, said inferior attachment system including a plurality of wall engaging members.

25. The system of claim 17, said graft delivery system further comprising:
 a balloon catheter assembly, said balloon catheter assembly is configured coaxially within said capsule assembly arrangement and adapted to engage said graft in order to seat said graft within the lumen.

26. The system of claim 17, said occlusive device delivery system further comprising an occlusive device capsule assembly, said occlusive device capsule assembly configured to releasably retain said occlusive device.

27. The system of claim 26, said occlusive device delivery system further comprising a tubular member extending proximally therefrom, said tubular member attached to a handle, said handle including a rotatable knob, the rotation of which causes said capsule assembly to move longitudinally with respect to said occlusive device.

28. The system of claim 17, said occlusive device further comprising an inverted tube which is configured at an opening formed in said first end.

29. The system of claim 17, said occlusive device further comprising an expandable attachment system attached to said second end, said attachment system including a plurality of wall engaging members.

30. An endovascular repair system, comprising:
- a graft, said graft including a plurality of V-shaped members having legs terminating in hooked ends attached to said graft;
- a graft delivery system, said graft delivery system adapted to deploy said graft within a first vascular lumen;
- an occlusive device; and
- an occlusive device delivery system, said occlusive device delivery system adapted to intraluminally deploy said occlusive device within a second vascular lumen.

31. The system of claim 30, wherein said graft has a main tubular body extending from a superior end and an inferior tubular portion extending from said main tubular body and defining an inferior end, said graft having a diameter which tapers from said main tubular body to said inferior tubular portion.

32. The system of claim 30, wherein the system is configured to deploy said graft and said occlusive device near a bifurcation in the corporeal lumen, said graft placed in a main branch feeding a plurality of branches and extending into one of said branches, said occlusive device placed in another of said branches.

33. The system of claim 30, said graft delivery system further comprising:
- an inferior capsule assembly; and
- a superior capsule assembly;
- wherein said inferior capsule assembly releasably retains an inferior end of said graft and said superior capsule assembly releasably retains a superior end of said graft.

34. The system of claim 33, said inferior capsule assembly being attached to a handle by an elongate tubular member, said handle including a rotatable knob, the rotation of which causes said inferior capsule to move longitudinally with respect to said handle.

35. The system of claim 33, said superior capsule assembly being attached to a handle by an elongate member, said handle including a rotatable knob, the rotation of which causes said superior capsule to move longitudinally with respect to said handle.

36. The system of claim 30, said graft further including an expandable superior attachment system attached to a superior end of said graft, said superior attachment system including a plurality of wall engaging members.

37. The system of claim 30, said graft further including an expandable inferior attachment system attached to an inferior end of said graft, said inferior attachment system including a plurality of wall engaging members.

38. The system of claim 30, said graft delivery system further comprising:
- a balloon catheter assembly said balloon catheter assembly adapted to engage said graft in order to seat said graft within the lumen.

39. The system of claim 30, said occlusive device delivery system further comprising an occlusive device capsule assembly, said occlusive device capsule assembly configured to releasably retain said occlusive device.

40. The system of claim 39, said occlusive device delivery system further comprising a tubular member extending proximally therefrom, said tubular member attached to a handle, said handle including a rotatable knob, the rotation of which causes said capsule assembly to move longitudinally with respect to said occlusive device.

41. The system of claim 30, said occlusive device further comprising an inverted tube which is configured at an opening formed in said first end.

42. The system of claim 30, said occlusive device further comprising an expandable attachment system attached to said second end, said attachment system including a plurality of V-shaped members having legs terminating in hooked.

43. A system for repair of a corporeal lumen, comprising:
- a graft including at least one V-shaped member having legs terminating in hooked ends;
- a graft delivery system adapted to intraluminally deploy said graft and including a balloon catheter assembly;
- an occlusive device, said occlusive device having a first and a second end, said second end defined by an opening providing access to an interior of said occlusive device; and
- an occlusive device delivery system, said occlusive device delivery system adapted to intraluminally deploy said occlusive device.

44. The system of claim 43, wherein said graft has a main tubular body extending from a superior end and an inferior tubular portion extending from said main tubular body and defining an inferior end.

45. The system of claim 43, wherein the system is configured to deploy said graft and said occlusive device near a bifurcation in the corporeal lumen, said graft placed in a main branch feeding a plurality of branches and extending into one of said branches, said occlusive device placed in another of said branches.

46. The system of claim 43, said graft delivery system further comprising:
- an inferior capsule assembly; and
- a superior capsule assembly;
- wherein said inferior capsule assembly releasably retains an inferior end of said graft and said superior capsule assembly releasably retains a superior end of said graft, said inferior and superior capsule assemblies being configured to move longitudinally relative to said graft in order to permit said graft to be deployed within the corporeal lumen.

47. The system of claim 46, said inferior capsule assembly being attached to a handle by an elongate tubular member, said handle including a rotatable knob, the rotation of which causes said inferior capsule to move longitudinally with respect to said handle.

48. The system of claim 46, said superior capsule assembly being attached to a handle by an elongate member, said handle including a rotatable knob, the rotation of which causes said superior capsule to move longitudinally with respect to said handle.

49. The system of claim 43, said graft further including an expandable superior attachment system attached to a superior end of said graft, said superior attachment system including a plurality of hooks.

50. The system of claim 43, said graft further including an expandable inferior attachment system attached to an inferior end of said graft, said inferior attachment system including a plurality of hooks.

51. The system of claim 43, said graft delivery system further comprising:
- a capsule jacket assembly; and
- wherein said capsule jacket assembly is configured to cover said graft during advancement of said graft within the corporeal lumen in order to permit deployment of said graft within the corporeal lumen and said balloon catheter assembly is configured coaxially within said capsule jacket assembly.

52. The system of claim 51, said occlusive delivery device further comprising an occlusive device capsule assembly, said occlusive device capsule assembly configured to releasably retain said occlusive device.

53. The system of claim 52, said occlusive device delivery system further comprising a tubular member extending proximally therefrom, said tubular member attached to a handle, said handle including a rotatable knob, the rotation of which causes said capsule assembly to move longitudinally with respect to said occlusive device.

54. The system of claim 43, said occlusive device further comprising an inverted tube which is configured at an opening formed in said first end.

55. The system of claim 43, said occlusive device further comprising an expandable attachment system attached to said second end, said attachment system including a generally sinusoidal frame and a plurality of V-shaped members having legs terminating in hooked ends, said V-shaped members being interspaced between struts defining said frame.

\* \* \* \* \*

UNITED STATES PATENT AND TRADEMARK OFFICE
CERTIFICATE OF CORRECTION

PATENT NO. : 6,287,330 B1
DATED : September 11, 2001
INVENTOR(S) : Peter K. Johansson et al.

It is certified that error appears in the above-identified patent and that said Letters Patent is hereby corrected as shown below:

<u>Title page</u>,
Item [56], References Cited, OTHER PUBLICATIONS, add the following:
-- Bettmann, Michael A,; M.D.; Scientific Sessions; pp. 161-202; CARDIOVASCULAR --.

<u>Column 32</u>,
Line 4, after "hooked", add -- ends --.

Signed and Sealed this

Seventeenth Day of February, 2004

JON W. DUDAS
*Acting Director of the United States Patent and Trademark Office*